United States Patent [19]

Yagihara et al.

[11] Patent Number: 4,518,685
[45] Date of Patent: May 21, 1985

[54] SILVER HALIDE PHOTOGRAPHIC LIGHT-SENSITIVE MATERIAL

[75] Inventors: Morio Yagihara; Akihiko Ikegawa; Mitsunori Ono; Yuji Mihara, all of Kanagawa, Japan

[73] Assignee: Fuji Photo Film Co., Ltd., Kanagawa, Japan

[21] Appl. No.: 601,402

[22] Filed: Apr. 17, 1984

[30] Foreign Application Priority Data

Apr. 18, 1983 [JP] Japan .................................. 58/68007

[51] Int. Cl.$^3$ .......................... G03C 1/46; G03C 1/02
[52] U.S. Cl. .................................. 430/505; 430/448; 430/544; 430/566; 430/570; 430/607; 430/955; 430/957; 430/958; 430/959; 430/960
[58] Field of Search ............... 430/955, 956, 957, 958, 430/959, 960, 443, 448, 505, 544, 218, 219, 239, 240, 566, 570, 607

[56] References Cited

U.S. PATENT DOCUMENTS

| | | | |
|---|---|---|---|
| 4,350,754 | 9/1982 | Bartels-Keith et al. | 430/505 |
| 4,371,604 | 2/1983 | Van de Sande et al. | 430/505 |
| 4,395,477 | 7/1983 | Abel | 430/505 |
| 4,420,554 | 12/1983 | Ohashi et al. | 430/955 |
| 4,481,277 | 11/1984 | Pfingston | 430/505 |

Primary Examiner—Mary F. Downey
Attorney, Agent, or Firm—Sughrue, Mion, Zinn, Macpeak & Seas

[57] ABSTRACT

A silver halide photographic light-sensitive material which comprises a support having thereon a light-sensitive silver halide emulsion layer, wherein the photographic light-sensitive material contains a blocked photographic agent therein represented by formula (I):

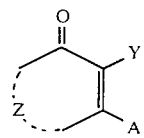

wherein A represents a photographic agent moiety which is bonded to a blocking moiety through a hetero atom or a group which is bonded to a blocking moiety through a hetero atom and capable of releasing a photographic agent upon a subsequent reaction after the group is released; Y represents a hydrogen atom or a substituent; and Z represents an atomic group necessary to form a carbocyclic ring or a heterocyclic ring.

The precursor of photographic agent is completely stable during the preservation of the photographic light-sensitive material and releases a photographic agent at a desired time upon the processing of the photographic light-sensitive material. The precursor also exhibits its function to a substantial degree over a wide range of pH.

34 Claims, No Drawings

SILVER HALIDE PHOTOGRAPHIC LIGHT-SENSITIVE MATERIAL

FIELD OF THE INVENTION

The present invention relates to a silver halide photographic light-sensitive material and, more particularly, to a silver halide photographic light-sensitive material containing a precursor compound of a photographically useful agent in which the active group is blocked.

BACKGROUND OF THE INVENTION

Photographically useful agents that are previously incorporated in a photographic light-sensitive material such that their effects will be produced at the appropriate time contain various features different from those which are used as an addition to a processing solution. Specific examples of the features in the former case are as follows: The incorporation in a photographic light-sensitive material enables effective utilization of photographic agents of the kind which tend to decompose under the acid-alkaline or the oxidation-reduction condition, and consequently, can not withstand long-time storage, in a processing bath. At the same time, such makes it possible to simplify the composition of the processing solution to be employed therewith and thereby to facilitate the preparation of the processing solution. Further, this makes it possible to force a required photographic agent to function in desired time during the photographic processing or at only the desired place, that is, in only a specified layer and the neighboring layers of a multilayer photographic light-sensitive material. Furthermore, this permits the presence of a photographic agent in the photographic light-sensitive material in such an amount as to vary as the function of silver halide development. However, if a photographic agent is added to a photographic light-sensitive material in its active form, it becomes impossible to make the photographic agent exhibit its ability to the expected degree because during storage before photographic processing, it reacts with other components contained in the photographic light-sensitive material or it is decomposed by heat, oxygen or so on.

One method for solving the above-described problem involves adding a photographic agent to a a photographic light-sensitive material in such a form that its active group is blocked and turned photographically inactive, that is, in the form of its precursor. Such a method can have various advantages in various cases to which it is applicable. For instance, in the case where the useful photographic agent is a dye, blocking a functional group of the dye which has a great effect on its spectral adsorption characteristic results in a shift of its spectral absorption band to shorter wavelengths or to longer wavelengths and therefore, even if the dye is present in a silver halide emulsion layer having the spectral sensitivity in the wavelength region corresponding to the absorption band which the dye has in the unblocked state, a lowering of the sensitivity due to the so-called filter effect can be prevented.

In another case where the useful photographic agent is an anti-foggant or a development restrainer, blocking of their active groups makes it possible to suppress desensitization arising from adsorption of these agents to light-sensitive silver halide grains and formation of silver salts upon storage. At the same time, release of these agents at required times permits the reduction of fog density without being attended by decrease in the sensitivity, the prevention of fog due to overdevelopment, development stoppage at a desired time, and so on.

In still another case where the useful photograpic agent is a developing agent, an auxiliary developing agent or a fogging agent, if their active or adsorptive groups are blocked, various photographically adverse effects which arise from semiquinones and oxidants produced by air oxidation upon storage can be prevented. Generation of fogging nuclei upon storage can also be prevented because injection of electrons into the silver halide grains can be inhibited. Therefore, stable processings can be effected therein.

In a further case that the useful photographic agent is a bleach accelerating agent or a bleach-fix accelerating agent, it also becomes possible to prevent reactions, with other components copresent in the photographic light-sensitive material, from occuring upon storage by blocking its active group and that, to make its expected ability bring into full play at a desired time by removing the blocking group.

In the present invention the above-described active group, functional group and adsorptive group are generally referred to as active group.

As described above, a precursor of photographic agents can be utilized as an extremely valuable tool in bringing out the abilities of the photographic agents to the best advantage. However, their precursor must satisfy very severe requirements for practical use. That is, the precursor must satisfy two requirements contradictory to each other; one is ensuring stable presence of the precursor under a storage condition, and the other is setting its blocking group loose at a desired time upon the processing and releasing the photographic agent rapidly and efficiently.

A number of techniques for blocking a photographic agent have already been known. For instance, a technique using a blocking group such as an acyl group, a sulfonyl group or the like is described in Japanese Patent Publication No. 44805/72 (corresponding to U.S. Pat. No. 3,615,617): one which utilizes such a blocking groups as to release a photographic agent by the so-called reversal Michel's reaction is described in Japanese Patent Publication Nos. 39727/79 (corresponding to U.S. Pat. No. 3,674,478), 9696/80 (corresponding to U.S. Pat. No. 3,791,830) and 34927/80 (corresponding to U.S. Pat. No. 4,009,029): one which utilizes such a blocking group as to release a photographic agent with the production of quinone methide or its analogs by intramolecular electron transfer is described in Japanese Patent Publication No. 39727/79, Japanese Patent Application (OPI) Nos. 135944/82, 135945/82 and 136640/82: one which utilizes an intramolecular ring-closing reaction is described in Japanese Patent Application (OPI) No. 53330/80: one which utilizes cleavage of a 5-membered or 6-membered ring is described in Japanese Patent Application (OPI) Nos. 76541/82 (corresponding to U.S. Pat. No. 4,335,200), 135949/82 and 179842/82: and so on. However, these photographic agents blocked with known blocking groups suffer from the defect that, for example, although stable under a storage condition, some precursors require a high alkaline condition, such as a pH higher than 12, for processing because the photographic agent-releasing rate thereof is too slow; some precursors decompose gradually to cause a failure of their function as the precursor under a storage condition, even though it can release the photographic agent at a sufficiently fast rate by processing under mild conditions such as in a pH range of 9 to 11; some precursors allow little latitude in controlling the rate of releasing the photographic agent therefrom and therefore, it requires a very narrow pH range for effecting the processing; and so on.

SUMMARY OF THE INVENTION

An object of the present invention is, therefore, to provide a precursor of a photographic agent which is completely stable under storage conditions and can release the photographic agent at a desired time upon processing.

Another object of the present invention is to provide a precursor of a photographic agent which can exhibit its function to a substantial degree over a wide pH range.

Other objects of the present invention will become apparent from the following detailed description and examples.

These objects of the present invention are attained by a silver halide photographic light-sensitive material which comprises a support having thereon a light-sensitive silver halide emulsion layer, wherein the photographic light-sensitive material therein contains a blocked photographic agent represented by formula (I):

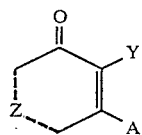

(I)

wherein A represents a photographic agent moiety which is bonded to a blocking moiety through a hetero atom or a group which is bonded to a blocking moiety through a hetero atom and capable of releasing a photographic agent upon a subsequent reaction after the group is released; Y represents a hydrogen atom or a substituent; and Z represents an atomic group necessary to form a carbocyclic ring or a heterocyclic ring.

DETAILED DESCRIPTION OF THE INVENTION

More specifically, the blocked photographic agent represented by the above-described general formula (I) can be represented by formula (I'):

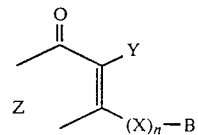

(I')

wherein
B represents a photographic agent moiety which is bonded to a blocking moiety through a hetero atom;
X represents a divalent linking group; n represents 0 or 1;
Y represents a hydrogen atom or a substituent; and
Z represents an atomic group necessary to form a carbocyclic ring or a heterocyclic ring.

In the above-described formulae, the substituent represented by Y includes a hydrogen atom, a halogen atom, an alkyl group, an alkenyl group, an aryl group, an alkoxy group, an aryloxy group, an acyloxy group, a carbonic acid ester group, an amino group, a carbonamido group, a ureido group, a carboxy group, an oxycarbonyl group, a carbamoyl group, an acyl group, a sulfo group, a sulfonyl group, a sulfamoyl group, a cyano group and a nitro group, etc.

Useful photographic agents, a monovalent residue of which is represented by B in above-described formula (I'), are known photographic agents which have at least one hetero atom and enter into combination with the blocking moiety through the hetero atom. Suitable examples of the photographic agent which can be employed in the present invention include antifoggants and development restrainers such as mercaptotetrazoles, mercaptotriazoles, mercaptopyrimidines, mercaptobenzimidazoles, mercaptoimidazoles, mercaptothiadiazoles, benzotriazoles, indazoles, etc.; developing agents such as p-phenylenediamines, hydroquinones, p-aminophenols, etc.; auxiliary developing agents such as pyrazolidones; fogging agents such as hydrazines, hydrazides, etc.; silver halide solvents such as hypo (i.e., sodium thiosulfate), etc.; bleach accelerating agents such as aminoalkylthiols, etc.; and dyes such as azo dyes, azomethine dyes, etc. In addition, photographic agents of the kind which further possess a redox function as to enable the release of the photographic agents as described above as a function of silver halide development, for example, coloring materials for color diffusion transfer photographic materials and DIR (development inhibitor releasing) hydroquinones, can also be employed as useful photographic agents.

The above-described useful photographic agents may be bonded directly (when n=0 in the general formula (I')) to the blocking moiety through their hetero atom, or may be bonded via X (when n=1 in the general formula (I')) to the blocking moiety.

X represents a divalent linking group, which is bonded to the blocking moiety through a hetero atom contained therein. The bond formed between X and the blocking moiety is cleaved upon the processing, and the resulting X-B splits per se promptly to release a photographic agent corresponding to B. Specific examples of the linking group of the above-described kind include ones which release the photographic agent by an intramolecular ring-closing reaction, as described in U.S. Pat. No. 4,248,962 (corresponding to British Patent Application (OPI) No. 2,010,818A): ones which release the photographic agent through intramolecular electron transfer, as described in U.S. Pat. No. 4,409,323, U.S. Pat. No. 4,421,845, etc.: ones which release the photographic agent with the evolution of carbon dioxide, as described in Japanese Patent Application (OPI) No. 179842/82: a divalent linking group (—OCH$_2$— group) which releases the photographic agent with the evolution of formaldehyde: and so on.

Structural formulae of representatives of X are illustrated below:

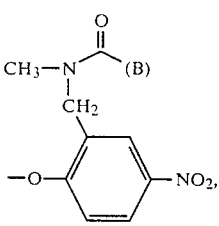

-continued

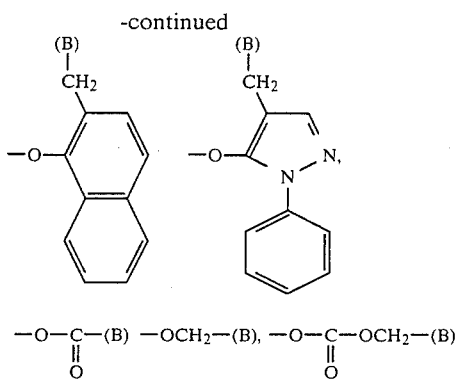

—O—C—(B)   —OCH$_2$—(B),   —O—C—OCH$_2$—(B)
      ‖                               ‖
      O                               O

In the above-described general formula (I) or (I') Y represents a hydrogen atom, a halogen atom (for example, a fluorine atom, a chlorine atom, a bromine atom, etc.), an alkyl group (preferably having from 1 to 20 carbon atoms), an alkenyl group (preferably having 2 to 20 carbon atoms), an aryl group (preferably having from 6 to 20 carbon atoms), an alkoxy group (preferably having from 1 to 20 carbon atoms), an aryloxy group (preferably having from 6 to 20 carbon atoms), an acyloxy group (preferably having from 2 to 20 carbon atoms), an amino group (including an unsubstituted amino group and preferably a secondary or a tertiary amino group substituted with an alkyl group having from 1 to 20 carbon atoms or an aryl group having from 6 to 20 carbon atoms), a carbonamido group (preferably an alkylcarbonamido group of which alkyl moiety has from 1 to 20 carbon atoms or an arylcarbonamido group of which aryl moiety has from 6 to 20 carbon atoms), a ureido group (preferably an alkylureido group of which alkyl moiety has from 1 to 20 carbon atoms or an arylureido group of which aryl moiety has from 6 to 20 carbon atoms), a carboxy group, a carbonic acid ester group (preferably an alkyl carbonic acid ester of which alkyl moiety has from 1 to 20 carbon atoms or an aryl carbonic acid ester of which aryl moiety has from 6 to 20 carbon atoms), an oxycarbonyl group (preferably an alkyloxycarbonyl group of which alkyl moiety has from 1 to 20 carbon atoms or an aryloxycarbonyl group of which aryl moiety has from 6 to 20 carbon atoms), a carbamoyl group (preferably an alkylcarbamoyl group of which alkyl moiety has from 1 to 20 carbon atoms or an arylcarbamoyl group of which aryl moiety has from 6 to 20 carbon atoms), an acyl group (preferably an alkylcarbonyl group of which alkyl moiety has from 1 to 20 carbon atoms or an arylcarbonyl group of which aryl moiety has from 6 to 20 carbon atoms), a sulfo group, a sulfonyl group (preferably an alkylsulfonyl group having from 1 to 20 carbon atoms or an arylsulfonyl group having from 6 to 20 carbon atoms), a sulfamoyl group (preferably an alkylsulfamoyl group having from 1 to 20 carbon atoms or an arylsulfamoyl group having from 6 to 20 carbon atoms), a cyano group or a nitro group. The above-described alkyl, alkenyl and aryl moieties respectively include those which are further substituted with the above-described various kinds of substituents.

The ring formed with Z includes, for example, a 5-membered, 6-membered or 7-membered carbocyclic ring, a 5-membered, 6-membered or 7-membered heterocyclic ring containing one or more nitrogen atoms, oxygen atoms or sulfur atoms or a condensed ring of the carbocyclic ring or heterocyclic ring. Specific examples of the ring to be used include cyclopentenone, cyclohexenone, cycloheptenone, benzocycloheptenone, 4-pyridone, 4-quinolone, 2-pyrone, 4-pyrone, 1-thio-2-pyrone, 1-thio-4-pyrone, coumarin, chromone, uracil, etc.

The carbocyclic ring or heterocyclic ring formed with Z may be substituted with one or more substituents and when two or more substituents are presnet they may be the same or different. Specific examples of the substituents include a halogen atom (for example, a fluorine atom, a chlorine atom, a bromine atom, etc.), an alkyl group (preferably having from 1 to 20 carbon atoms), an aryl group (preferably having from 6 to 20 carbon atoms), an alkoxy group (preferably having from 1 to 20 carbon atoms), an aryloxy group (preferably having from 6 to 20 carbon atoms), an acyl group (preferably having from 2 to 20 carbon atoms), an acylamino group (preferably an alkanoylamino group of which alkyl moiety has from 1 to 20 carbon atoms or a benzoylamino group of which aryl moiety has from 6 to 20 carbon atoms), a nitro group, a cyano group, an oxycarbonyl group (preferably an alkoxycarbonyl group of which alkyl moiety has from 1 to 20 carbon atoms or an aryloxycarbonyl group of which aryl moiety has from 6 to 20 carbon atoms), a hydroxy group, a carboxy group, a sulfo group, a ureido group (preferably an alkylureido group of which alkyl moiety has from 1 to 20 carbon atoms or an arylureido group of which aryl moiety has from 6 to 20 carbon atoms), a sulfonamido group (preferably an alkylsulfonamido group having from 1 to 20 carbon atoms or an arylsulfonamido group having from 6 to 20 carbon atoms), a sulfamoyl group (preferably an alkylsulfamoyl group having from 1 to 20 carbon atoms or an arylsulfamoyl group having from 6 to 20 carbon atoms), a carbamoyl group (preferably an alkylcarbonyl group of which alkyl moiety has from 1 to 20 carbon atoms or an arylcarbamoyl group of which aryl moiety has from 6 to 20 carbon atoms), an acyloxy group (preferably having from 2 to 20 carbon atoms), an amino group (including an unsubstituted amino group and preferably a secondary or a tertiary amino group substituted with an alkyl group having from 1 to 20 carbon atoms or an aryl group having from 6 to 20 carbon atoms), a carbonic acid ester group (preferably an alkyl carbonic acid ester of which alkyl moiety has from 1 to 20 carbon atoms or an aryl carbonic acid ester of which aryl moiety has from 6 to 12 carbon atoms), a sulfone group (preferably an alkylsulfone group having from 1 to 20 carbon atoms or an arylsulfone group having from 6 to 20 carbon atoms), etc.

Of the compounds represented by the general formula (I'), a cyclopentenone compound represented by the general formula (II) described below and an uracil compound represented by the general formula (III) described below are particularly preferred.

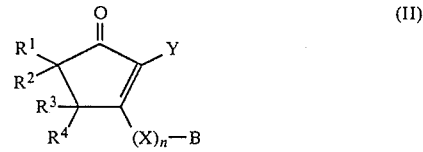

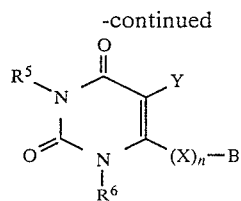
(III)

wherein B, X, Y and n each has the same meaning as defined in the general formula (I'); and $R^1$, $R^2$, $R^3$, $R^4$, $R^5$ and $R^6$ each has the same meaning as a group defined for the substituent of the carbocyclic ring or heterocyclic ring formed with Z.

Further, the substituent Y is selected depending upon the pH of a processing solution to be employed for the processing the photographic light-sensitive material in which the precursor of the photographic agent according to the present invention is incorporated, and upon the time required for timing. For example, when a processing solution having a high pH is used, or when slow timing is required, an electron donating group e.g., an alkyl group, an alkoxy group, etc. is selected as Y, whereas if fast timing is required or the processing is carried out under mild alkaline conditions having a pH of 9 to 11, an electron attracting group e.g., a halogen atom, an acyl group, a sulfonyl group, a cyano group, a nitro group, etc. is selected as Y, thus achieving the desired purpose. In the above-described manner, it is feasible to control the releasing rate over a very wide range by choosing a proper group for Y.

Specific examples of the useful blocked photographic agents according to the present invention are set forth below, but the present invention should not be construed as being limited thereto.

Compound (1)

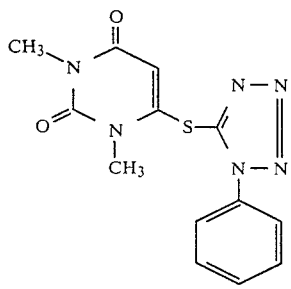

Compound (2)

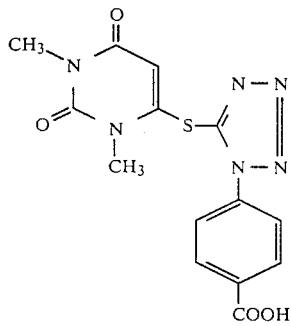

Compound (3)

Compound (3)

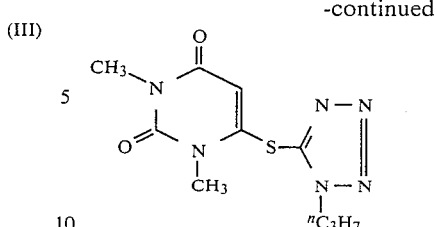

Compound (4)

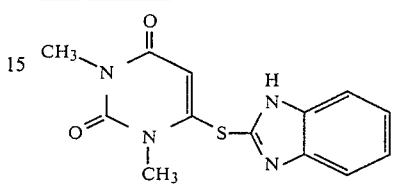

Compound (5)

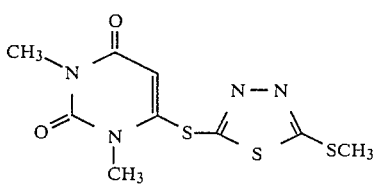

Compound (6)

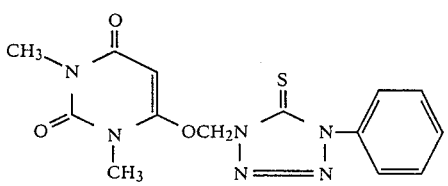

Compound (7)

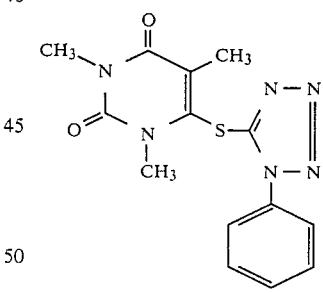

Compound (8)

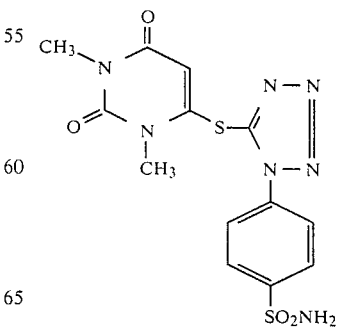

Compound (9)

-continued
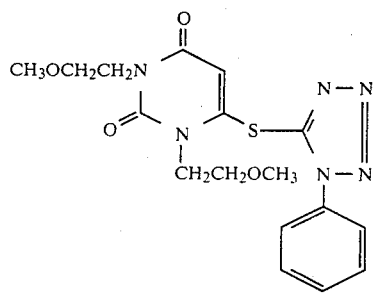
Compound (10)
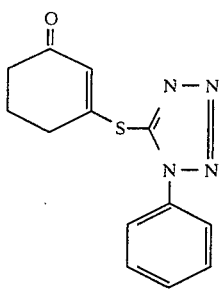
Compound (11)
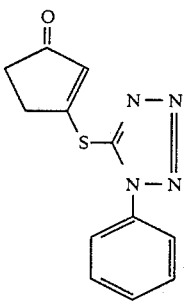
Compound (12)
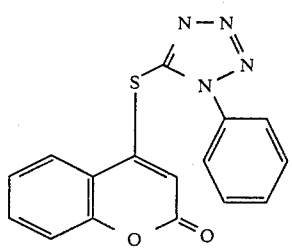
Compound (13)
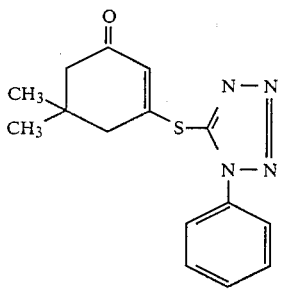
Compound (14)
-continued
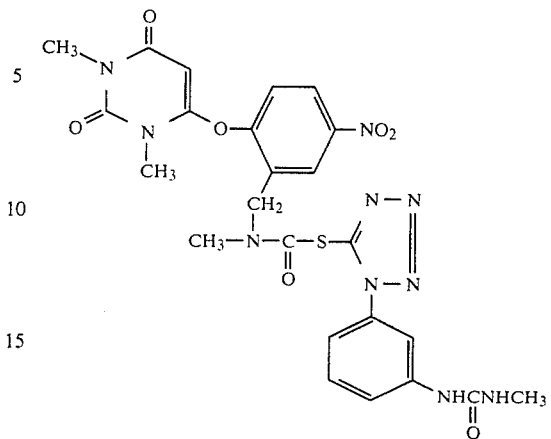
Compound (15)
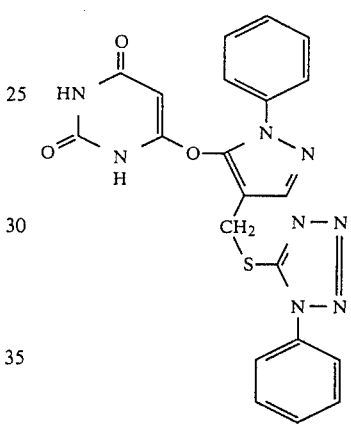
Compound (16)
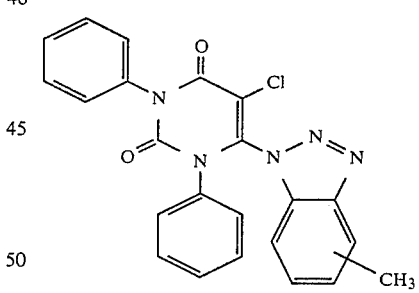
Compound (17)
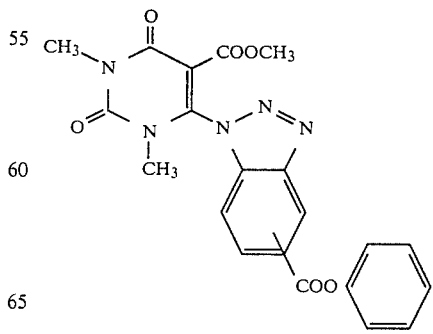
Compound (18)

-continued
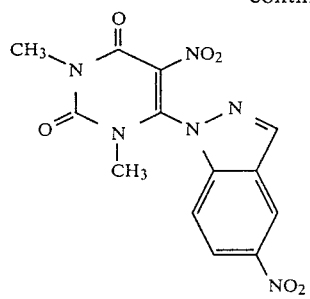
Compound (19)
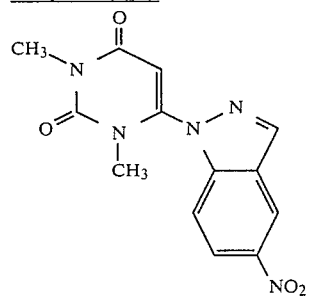
Compound (20)
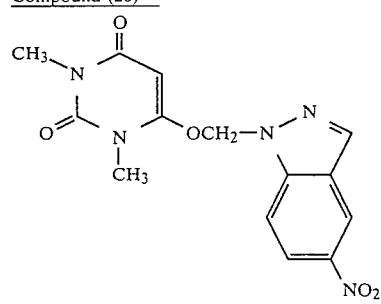
Compound (21)
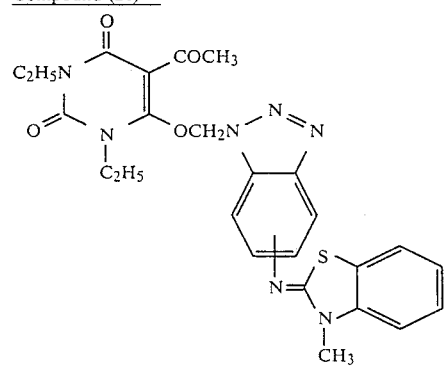
Compound (22)
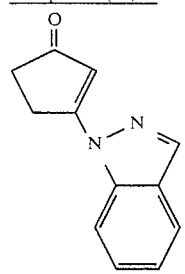
Compound (23)
-continued
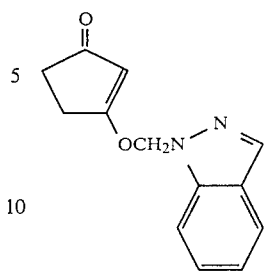
Compound (24)
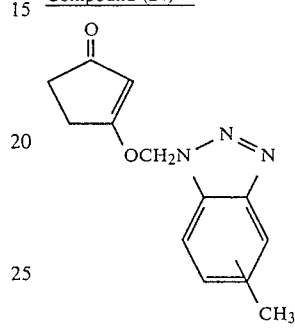
Compound (25)
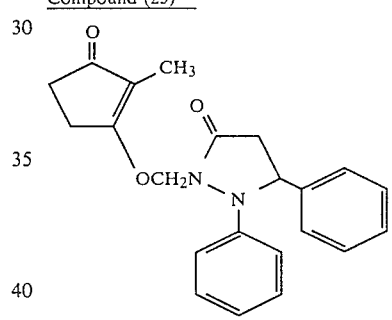
Compound (26)
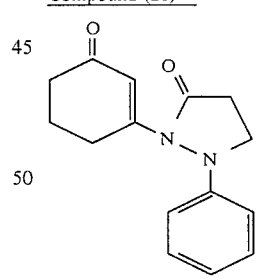
Compound (27)
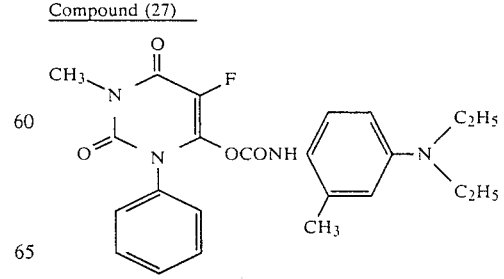
Compound (28)

-continued

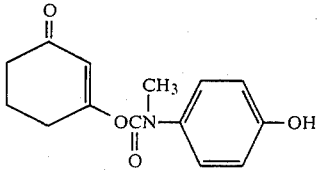

Compound (29)

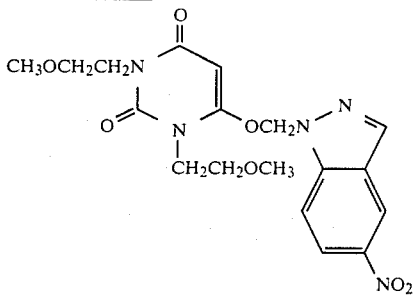

Compound (30)

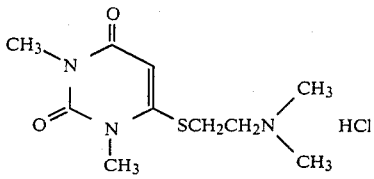

(31)

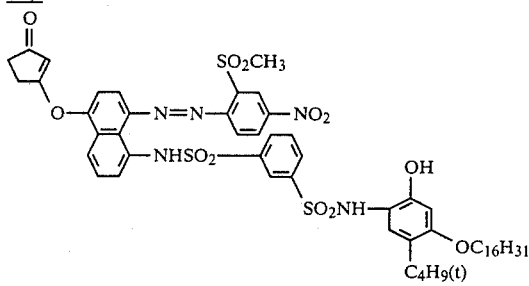

Typical synthesis examples of the blocked photographic agent according to the present invention are shown below.

SYNTHESIS EXAMPLE 1

Synthesis of Compound (1)

6-Chloro-1,3-dimethyluracil was synthesized according to the method as described in *Liebigs Ann. Chem.*, Bd. 612, page 161 (1958) in the following manner.

276 g (3.14 mol) of 1,3-dimethylurea and 376 g (3.62 mol) of malonic acid were dissolved in 600 ml of glacial acetic acid at 60° to 70° C. To the solution was added 1250 ml of acetic anhydride and the temperature was gradually raised to 90° C. After stirring for 6 hours, the reaction mixture was allowed to stand at room temperature overnight and the glacial acetic acid and acetic anhydride were distilled off under reduced pressure. The residue was poured into 500 ml of ethanol while it was still hot, the crystals thus-deposited were collected by filtration and refluxed by heating in a mixture of 380 ml of concentrated hydrochloric acid and 400 ml of water for 2 hours. The mixture was allowed to stand under cooling with ice for 6 hours, the crystals thus-deposited were collected by filtration and washed with a small amount of ethanol to obtain 360 g of 1,3-dimethylbarbituric acid. Yield: 73%, Melting Point: 124° to 125° C.

To 110 g of 1,3-dimethylbarbituric acid thus-obtained was added 32 ml of water and then 800 ml of phosphorus oxychloride was gradually added dropwise. The mixture was refluxed by heating for 1.5 hours, the phosphorus oxychloride was distilled off under normal pressure and the residue was poured onto ice while it was still hot. The crystals thus-deposited were collected by filtration, the filtrate was extracted 3 times with chloroform and dried with anhydrous sodium sulfate. The chloroform was distilled off and the residue thus-obtained were recrystallized from water together with the crystals obtained above to obtain 80 g of 6-chloro-1,3-dimethyluracil. Yield: 64%, Melting Point: 113° to 115° C.

To 20 ml of a methanol solution containing 1.78 g (0.01 mol) of 5-mercapto-1-phenyltetrazole was added 1.93 g (0.01 mol) of a 28% methanol solution of sodium methylate, the mixture was stirred at room temperature for 5 minutes and then the methanol was distilled off under reduced pressure. The residue thus-obtained was dissolved in 30 ml of tetrahydrofuran, to which was added 1.75 g (0.01 mol) of 6-chloro-1,3-dimethyluracil described above and the mixture was refluxed by heating for 24 hours. The reaction solution was poured into ice water, the crystals thus-deposited were collected by filtration and recrystallized from methanol to obtain 1.60 g of Compound (1). Yield: 51%, Melting Point: 170° C. (decomp.).

Elemental Analysis for $C_{13}H_{12}N_6O_2S$: Calculated; C: 49.35%, H: 3.82%; N: 26.57%. Found; C: 49.35%; H: 3.95%; N: 26.53%.

SYNTHESIS EXAMPLE 2

Synthesis of Compound (2)

To 40 ml of an N,N-dimethylacetamide solution containing 2.22 g (0.01 mol) of 1-(4-carboxyphenyl)-5-mercaptotetrazole were added 4.1 ml (0.03 mol) of triethylamine at room temperature and then 1.75 g (0.01 mol) of 6-chloro-1,3-dimethyluracil as described in Synthesis Example 1 and the mixture was stirred at 70° C. for 24 hours. The reaction solution was poured into ice water, the crystals thus-deposited were collected by filtration and recrystallized from a solvent mixture of acetone and hexane to obtain 1.50 g of Compound (2). Yield: 42%, Melting Point: 174° C. (decomp.)

Elemental Analysis for $C_{14}H_{12}N_6O_4S$; Calculated; C: 49.35%; H: 3.82%; N: 26.57%. Found; C: 48.95%; H: 3.65%; N: 26.09%.

SYNTHESIS EXAMPLE 3

Synthesis of Compound (4)

To 40 ml of a tetrahydrofuran solution containing 1.50 g (0.01 mol) of 2-mercaptobenzimidazole were added 10 ml of a tetrahydrofuran solution containing 1.67 g (0.011 mol) of 1,5-diazabicyclo[5,4,0]undecene-5 (DBU) at room temperature and then 10 ml of a methanol solution containing 1.75 g (0.01 mol) of 6-chloro-1,3-dimethyluracil as described in Synthesis Example 1 and the mixture was refluxed by heating for 11 hours. The reaction solution was poured into ice water, the crystals thus-deposited were collected by filtration and recrystallized from a solvent mixture of ethyl acetate and hexane to obtain 1.90 g of Compound (4). Yield: 66%, Melting Point: 194° to 195° C.

SYNTHESIS EXAMPLE 4

Synthesis of Compound (7)

75 g (0.85 mol) of 1,3-dimethylurea and 102 g (0.86 mol) of methyl malonic acid were dissolved in 300 ml of glacial acetic acid at 65° C. To the solution was added 330 ml of acetic anhydride, the temperature was gradually raised and the mixture was refluxed by heating at 90° C. for 6 hours. The reaction solution was concentrated under reduced pressure, and benzene was added to the residue. The crystals thus-deposited were collected by filtration and recrystallized from benzene to obtain 60 g of 1,3,5-trimethylbarbituric acid. Yield: 42%, Melting Point: 83° to 85° C.

To 34 g (0.2 mol) of 1,3,5-trimethylbarbituric acid thus-obtained was added 10 ml of water and then 250 ml of phosphorus oxychloride was gradually added dropwise. The mixture was refluxed by heating for 1.5 hours, the phosphorus oxychloride was distilled off under normal pressure and the residue was poured onto ice while it was still hot. The crystals thus-deposited were collected by filtration to obtain 25 g of 6-chloro-1,3,5-trimethyluracil.

Yield: 66%, Melting Point: 129° to 133° C.

To 20 ml of a methanol solution containing 1.78 g (0.01 mol) of 5-mercapto-1-phenyltetrazole was added 1.93 g (0.01 mol) of a 28% methanol solution of sodium methylate, the mixture was stirred at room temperature for 5 minutes and then the methanol was distilled off under reduced pressure. The residue thus-obtained was dissolved in 30 ml of tetrahydrofuran, to which was added 10 ml of a tetrahydrofuran solution containing 1.89 g (0.01 mol) of 6-chloro-1,3,5-trimethyluracil described above and the mixture was refluxed by heating for 48 hours. The reaction solution was poured into ice water, the crystals thus-deposited were collected by filtration and recrystallized from isopropanol to obtain 1.70 g of Compound (7).

Yield: 52%, Melting Point: 183° to 184° C.

Elemental Analysis for $C_{14}H_{14}N_6O_2S$: Calculated: C: 50.89%; H: 4.27%; N: 25.44%. Found; C: 50.89%; H: 4.20%; N: 25.60%.

SYNTHESIS EXAMPLE 5

Synthesis of Compound (8)

To 20 ml of a suspension of methanol containing 2.57 g (0.01 mol) of 5-mercapto-1-(4-sulfamoylphenyl)tetrazole was added 1.93 g of a 28% methanol solution containing sodium methylate at room temperature, the mixture was stirred for 5 minutes and the methanol was distilled off under reduced pressure. The residue was dissolved by adding thereto 30 ml of tetrahydrofuran and 5 ml of methanol, to the solution was added 1.75 g (0.01 mol) of 6-chloro-1,3-dimethyluracil as described in Synthesis Example 1 and the mixture was refluxed by heating for 48 hours. The reaction solution was poured into ice water, the crystals thus-deposited were collected by filtration and recrystallized from acetonitrile to obtain 2.80 g of Compound (8).

Yield: 71%, Melting Point: 183° C. (decomp.)

Elemental Analysis for $C_{13}H_{13}N_7O_4S_2$: Calculated; C: 39.48%; H: 3.31%; N: 24.80%. Found; C: 39.87%; H: 3.49%; N: 25.02%.

Elemental Analysis for $C_{13}H_{12}N_4O_2S$: Calculated; C: 54.15%; H: 4.19%; N: 19.44%. Found; C: 54.17%; H: 4.13%; N: 19.43%.

SYNTHESIS EXAMPLE 6

Synthesis of Compound (10)

To 100 ml of a suspension of benzene containing 20.0 g (0.18 mol) of cyclohexane-1,3-dione was added 24.2 g (0.18 mol) of phosphorus trichloride and the mixture was refluxed by heating for 1 hour. The solvent was distilled off under reduced pressure to obtain 19.2 g of 3-chloro-2-cyclohexen-1-one as a light yellow oily product.

Yield: 81%.

To 20 ml of a tetrahydrofuran solution containing 5.47 g (0.031 mol) of 5-mercapto-1-phenyltetrazole, 10 ml of glacial acetic acid and 5.03 g (0.06 mol) of sodium acetate was added with stirring 4.0 g (0.031 mol) of 3-chloro-2-cyclohexen-1-one obtained above and the mixture was stirred at 60° to 70° C. for 5 hours. The reaction solution was poured into ice water, extracted with ethyl acetate, then the organic layer was dried with anhydrous sodium sulfate and concentrated. The oily product thus-obtained was purified by silica gel column chromatography (eluate: ethyl acetate-hexane=1:4) to obtain 6.3 g of Compound (10) as white crystals. Yield: 75%, Melting Point: 69° to 71° C.

Elemental Analysis for $C_{13}H_{12}N_4OS$: Calculated; C: 57.33%; H: 4.44%; N: 20.58%. Found; C: 57.40%; H: 4.45%; N: 20.66%.

SYNTHESIS EXAMPLE 7

Synthesis of Compound (11)

To 200 ml of a chloroform solution containing 16 g of cyclopentane-1,3-dione was added 20 ml of phosphorus trichloride and the mixture was refluxed by heating for 5 hours. The reaction solution was poured into ice water and extracted 3 times with ethyl acetate. The organic layer was dried with anhydrous sodium sulfate, concentrated and the residue thus-obtained was distilled under reduced pressure to obtain 8 g of 3-chloro-2-cyclopenten-1-one as a colorless oily product. Yield: 42%, Boiling Point: 77° to 78° C. at 25 mmHg.

To 10 ml of tetrahydrofuran solution containing 1.2 g (0.011 mol) of 3-chloro-2-cyclopenten-1-one obtained above were added 1.78 g (0.01 mol) of 5-mercapto-1-phenyltetrazole, 1.64 g (0.02 mol) of sodium acetate and 40 ml of glacial acetic acid and the mixture was stirred at room temperature for 5 hours. The reaction mixture was poured into ice water, the crystals thus-deposited were collected by filtration and recrystallized from a solvent mixture of tetrahydrofuran and hexane to obtain 1.55 g of Compound (11). Yield: 60%, Melting Point: 115° to 116° C.

Elemental Analysis for $C_{12}H_{10}N_4OS$: Calculated; C: 55.80%; H: 3.90%; N: 21.70%. Found; C: 55.67%; H: 3.71%; N: 21.60%.

SYNTHESIS EXAMPLE 8

Synthesis of Compound (13)

To 200 ml of a chloroform solution containing 100 g (0.71 mol) of dimedone was added 21 ml of phosphorus trichloride and the mixture was refluxed by heating for 3 hours. To the reaction solution was added ice water to terminate the reaction, the chloroform was distilled off under reduced pressure and the aqueous layer was extracted with ethyl acetate. The organic layer was dried with anhydrous sodium sulfate, concentrated under reduced pressure and the residue was purified by distillation under reduced pressure to obtain 45 g of 3-chloro-5,5-dimethyl-2-cyclohexene-1-one. Yield: 40%, Boiling Point: 95° C. at 18 mmHg.

7 g (0.044 mol) of 3-chloro-5,5-dimethyl-2-cyclohexen-1-one was mixed with 50 ml of glacial acetic acid, 3.9 g of sodium acetate and 5.6 g of 5-mercapto-1-phenyltetrazole and the mixture was stirred at 80° C. for 6 hours. The reaction solution was poured into ice water, the crystals thus-deposited were collected by filtration and recrystallized from a solvent mixture of ethyl acetate and hexane to obtain 7.4 g of Compound (13).

Yield: 78%, Melting Point: 119° to 120° C.

Elemental Analysis for $C_{15}H_{16}N_4OS$: Calculated; C: 59.97%; H: 5.37%; N: 18.66%. Found; C: 60.01%; H: 5.30%; N: 18.59%.

SYNTHESIS EXAMPLE 9

Synthesis of Compound (18)

To 25 ml of surfuric acid was gradually added 8.5 g (0.049 mol) of 6-chloro-1,3-dimethyluracil as described in Synthesis Example 1. To the solution was gradually added at 0° to 5° C. 8.5 ml of fuming nitric acid and the mixture was stirred for 5 minutes. The reaction solution was poured onto ice and extracted twice with chloroform. The organic layer was dried with anhydrous magnesium sulfate, concentrated and the crystals thus-obtained were recrystallized from a solvent mixture of ethyl acetate and hexane to obtain 7.5 g of 6-chloro-1,3-dimethyl-5-nitrouracil.

Yield: 70%, Melting Point: 91° to 92° C.

To 40 ml of a tetrahydrofuran solution containing 1.79 g (0.011 mol) of 5-nitroindazole was added 10 ml of a tetrahydrofuran solution containing 1.67 g (0.011 mol) of 1,5-diazabicyclo[5,4,0]undesene-5 (DBU) at room temperature and the mixture was stirred for 5 minutes. To the mixture was added 2.20 g (0.01 mol) of 6-chloro-1,3-dimethyl-5-nitrouracil described above and the mixture was refluxed by heating for 15 hours. The reaction solution was poured into ice water, the crystals thus deposited were collected by filtration and recrystallized from ethanol to obtained 1.1 g of Compound (18). Yield: 32%, Melting Point: 157° to 160° C.

Elemental Analysis for $C_{13}H_{10}N_6O_6$: Calculated; C: 45.09%; H: 2.91%; N: 24.28%. Found; C: 45.38; H: 3.12% N: 23.99%.

The precursors according to the present invention may be used in combination with two or more thereof.

The blocked photographic agents (precursors) according to the present invention may be added to any constituent layers of a silver halide photographic light-sensitive material including a silver halide emulsion layer, a coloring material layer, a subbing layer, a protective layer, an interlayer, a filter layer, an antihalation layer, an image-receiving layer, a cover sheet layer and other subsidiary layers.

Incorporation of the precursors used in the present invention into the above-described layers can be carried out by adding them to coating solutions for forming such layers as they are, or in such a state that they are dissolved in a proper concentration in such a solvent as not to affect adversely the photographic light-sensitive material, such as water, alcohol or the like. Also, the precursors can be added in such a state that they are first dissolved in an organic solvent having a high boiling point and/or an organic solvent having a low boiling point and then, emulsified and dispersed in an aqueous solution. Moreover, they may be added in such a state that they are loaded into polymer latexes using the methods as described in Japanese Patent Application (OPI) Nos. 39853/76, 59942/76 and 32552/79, U.S. Pat. No. 4,199,363, etc.

The precursors may be added at any stages of the production of the photographic light-sensitive material. However, it is generally preferable to choose the stage of just before the coating.

A preferred addition amount of the compound according to the present invention is varied depending on the kind of the photographically useful agent which is the root thereof. For instance, in the case of an antifoggant or a development restrainer, a preferred addition amount of its precursor ranges from $10^{-8}$ mole to $10^{-1}$ mole per mole of silver. More specifically, in the case of the antifoggant of mercapto group-containing type it ranges from $10^{-6}$ mole to $10^{-1}$ mole per mole of silver and on the other hand, in case of the antifoggant of azole type, such as a benzotriazole, etc., it ranges from $10^{-5}$ mole to $10^{31\ 1}$ mole per mole of silver. In the case of a developing agent, a preferred addition amount of its precursor ranges from $10^{-2}$ mole to 10 mole, particularly from 0.1 mole to 5 mole, per mole of silver. In the case of an auxiliary developing agent of a pyrazolidone type, a preferred addition amount of its precursor ranges from $10^{-4}$ mole to 10 mole, particularly from $10^{-2}$ mole to 5 mole per mole of silver. In the case of a fogging agent, a preferred addition amount of its precursor ranges from $10^{-2}$ mole to $10^{-6}$ mole, particularly from $10^{-3}$ mole to $10^{-5}$ mole per mole of silver. In the case of a silver halide solvent such as hypo, etc., a preferred addition amount of its precursor ranges from $10^{-3}$ mole to 10 mole, particularly from $10^{-2}$ mole to 1 mole per mole of silver. In the case of a bleach accelerating agent such as aminoethanethiols, etc., a preferably addition amount of its precursor ranges from $10^{-5}$ mole to 0.1 mole, particularly from $10^{-4}$ to $10^{-2}$ mole, per mole of silver. In the case of a dye or a coloring material for color diffusion transfer photographic light-sensitive material, a preferred addition amount of its precursor ranges from $10^{-3}$ mole to 1 mole, particularly from $5 \times 10^{-3}$ mole to 0.5 mole per mole of silver.

The precursors of photographic agents according to the present invention are completely stable under storage conditions and can release the photographic agent at a desired time upon processing due to the blocking moiety shown in the general formulae (I) above. Further, according to the present invention an advantage is achieved in that the precursors of photographic agents which can exhibits their function over a wide pH range can be easily obtained by appropriate selection of the substituent represented by Y in the general formulae above. Moreover, photographic light-sensitive material containing the precursors of photographic agent according to the present invention in which the photographic agent moieties are antiffogants or development restrainers have an advantage in that the screen range is long when dot images are formed and thus they are particularly suitable for photographic light-sensitive materials for plate making.

The compounds according to the present invention can be employed for, for example, color photographic light-sensitive materials of the coupler type.

A general method for forming color images using a color photographic light-sensitive material comprises developing a silver halide light-sensitive material with an aromatic primary amine developing agent in the presence of color couplers which have such an ability as to form dyes by reacting with the oxidation products of developing agents, to produce azomethine dyes or indoaniline dyes. The basis of the above-described color development method was invented by L. D. Mannes & L. Godowsky in 1935 and thereafter, various improvements have been introduced thereinto. Nowadays, this color development method is universally employed in this art.

In this method, the substractive color process is usually employed for color reproduction, wherein silver halide emulsions which are sensitive selectively to blue, green and red lights respectively, and yellow, magenta and cyan color image-forming agents which bear their respective complementary relations to those lights are used. In order to form yellow color images, couplers of, e.g., acylacetanilide type or dibenzoylmethane type are used. In order to form magenta color images, couplers of pyrazolone type, pyrazolobenzimidazole type, cyanoacetophenone type or indazolone type are predominantly used. In order to form cyan color images, couplers of phenol type, e.g., phenols and naphthols, are predominantly used.

In general, color photographic light-sensitive materials are divided broadly into two main groups; one group consists of the coupler-in-developer type, which utilize couplers added to a developing solution, and the other group consists of those of the coupler-in-emulsion type, which contain couplers in their light-sensitive layers in such a state that the couplers may retain their own functions independently. In the latter materials, dye image-forming couplers are incorporated in silver halide emulsion layers. For couplers to be added to emulsion layers, it is necessary to be rendered nondiffusible (diffusion resistant) in the matrix of emulsion binder.

The processing steps of color photographic light-sensitive materials of the coupler-in-emulsion type comprises basically of the following three steps.

(1) Color development step
(2) Bleaching step
(3) Fixing step

A bleaching step and a fixing step may be carried out at the same time. That is, it is called a bleach-fixing (blixing) step, and both developed silver and undeveloped silver halide are desilvered in this step. Besides involving the above-described two basic steps, the color development step and the desilvering step, the actual processing for development processing includes auxiliary steps for the purposes of retaining the photographic and physical qualities of the image, improving the storability of the image, and so on. For instance, there are steps using a hardening bath for preventing light-sensitive films from being excessively softened during the processing, a stop bath for stopping a development reaction effectively, an image-stabilizing bath, a layer-removing bath for removing a backing layer from the support, and so on.

Couplers are added to or dispersed into gelatin-silver halide emulsions or hydrophilic colloid according to conventionally known methods. Specifically, a method of dispersing a coupler in the form of a mixture with an organic solvent having a high boiling point such as dibutyl phthalate, tricresyl phosphate, waxes, a higher fatty acid or its ester, etc. such a method as described in, e.g., U.S. Pat. Nos. 2,304,939 and 2,322,027, and so on; a method of dispersing a coupler in the form of a blend with an organic solvent having a low boiling point or a water soluble organic solvent; a method of dispersing a coupler in the form of a mixture with a combination of an organic solvent a high boiling point and an organic solvent having a low boiling point such a method as described in, e.g., U.S. Pat. Nos. 2,801,170, 2,801,171 and 2,949,360, and so on; a method of dispersing a coupler by itself or in combination with other couplers required for combined use, such as a colored coupler and an uncolored coupler, where the coupler per se has a low melting point (e.g., not higher than 75° C.) such a method as described in German Pat. No. 1,143,707, and so on can be employed.

Suitable examples of a dispersing aid which can be employed for dispersion of couplers include anionic surface active agents (e.g., sodium alkylbenzenesulfonates, sodium dioctylsulfosuccinate, sodium dodecylsulfate, sodium alkylnaphthalenesulfonates, Fischer type couplers, etc.), amphoteric surface active agents (e.g., N-tetradecyl-N,N-dipolyethylene-α-betaine, etc.) and nonionic surface active agents (e.g., sorbitan monolaurate, etc.).

Suitable couplers which can be used in combination with the compounds according to the present invention include known couplers as set forth below.

Specific examples of magenta color-forming couplers which can be used include those described in U.S. Pat. Nos. 2,600,788, 2,983,608, 3,062,653, 3,127,269, 3,311,476, 3,419,391, 3,519,429, 3,558,319, 3,582,322, 3,615,506, 3,834,908 and 3,891,445, West German Pat. No. 1,810,464, West German Patent Application (OLS) Nos. 2,408,665, 2,417,945, 2,418,959 and 2,424,467: Japanese Patent Publication No. 6031/65, Japanese Patent Application (OPI) Nos. 20826/76, 58922/77, 129538/74, 74027/74, 159336/75, 42121/77, 74028/74, 60233/75, 26541/76 and 55122/78, and so on.

Specific examples of yellow color-forming couplers which can be used include those described in U.S. Pat. Nos. 2,875,057, 3,265,506, 3,408,194, 3,551,155, 3,582,322, 3,725,072 and 3,891,445, West German Pat. No. 1,547,868, West German Patent Application (OLS) Nos. 2,219,917, 2,261,361 and 2,414,006, British Pat. No. 1,425,020, Japanese Patent Publication No. 10783/76, Japanese Patent Application (OPI) Nos. 26133/72, 73147/73, 102636/76, 6341/75, 123342/75, 130442/75, 21827/76, 87650/75, 82424/77 and 115219/77 and so on.

Specific examples of cyan color-forming couplers which can be used include those described in U.S. Pat. Nos. 2,369,929, 2,434,272, 2,474,293, 2,521,908, 2,895,826, 3,034,892, 3,311,476, 3,458,315, 3,476,563, 3,583,971, 3,591,383, 3,767,411 and 4,004,929, West German Patent Application (OLS) Nos. 2,414,830 and 2,454,329, Japanese Patent Application (OPI) Nos. 59838/73, 26034/76, 5055/73, 146828/76, 69624/77 and 90932/77 and so on.

Specific examples of colored couplers which can be used include those described in U.S. Pat. Nos. 3,476,560, 2,521,908 and 3,034,892, Japanese Patent Publication Nos. 2016/69, 22335/63, 11304/67 and 32461/69, Japanese Patent Application (OPI) Nos. 26034/76 and 42121/77, West German Patent Application (OLS) No. 2,418,959, and so on.

Specific examples of DIR couplers which can be used include those described in U.S. Pat. Nos. 3,227,554, 3,617,291, 3,701,783, 3,790,384 and 3,632,345: West German Patent Application (OLS) Nos. 2,414,006, 2,454,301 and 2,454,329, British Pat. No. 953,454, Japanese Patent Application (OPI) Nos. 69624/77 and 122335/74, Japanese Patent Publication No. 16141/76.

In addition to DIR couplers, compounds capable of releasing a development inhibitor with the progress of development may be incorporated in a photographic light-sensitive material. For example, compounds as described in U.S. Pat. Nos. 3,297,445 and 3,379,529, West German Patent Application (OLS) No. 2,417,914, Japanese Patent Application (OPI) Nos. 15271/77 and 9116/78, and so on can be used.

Suitable organic solvents having a high boiling point which can be used are those described in U.S. Pat. Nos. 2,322,027, 2,533,514 and 2,835,579, Japanese Patent Publication No. 23233/71, U.S. Pat. No. 3,287,134, British Pat. No. 958,441, Japanese Patent Application (OPI) No. 1031/72, British Pat. No. 1,222,753, U.S. Pat. No. 3,936,303, Japanese Patent Application (OPI) Nos. 26037/76 and 82078/75, U.S. Pat. Nos. 2,353,262, 2,852,383, 3,554,755, 3,676,137, 3,676,142, 3,700,454, 3,748,141 and 3,837,863, West German Patent Application (OLS) No. 2,538,889, Japanese Patent Application (OPI) Nos. 27921/76, 27922/76, 26035/76, 26036/76 and 62632/75, Japanese Patent Publication No. 29461/74, U.S. Pat. Nos. 3,936,303 and 3,748,141, Japanese Patent Application (OPI) No. 1521/78, and so on.

Upon the application to the color diffusion transfer photographic process, the photographic material of the present invention may constitute any type of film unit, including the peel-apart type, the integrated type as described in Japanese Patent Publication Nos. 16356/71 and 33697/73, Japanese Patent Application (OPI) No. 13040/75 and British Pat. No. 1,330,524, or the peel-apart unneeded type as described in Japanese Patent Application (OPI) No. 119345/82.

In any film units of the above-described formats, it is advantageous to provide a polymeric acid layer protected by a neutralization timing layer from the standpoint of extending the range of the processing temperatures.

The precursors represented by the above-described general formula (I) may be added to any layer of the film unit of the diffusion transfer photographic material, provided that they are associated with silver halide emulsions so as to act effectively upon the development of the silver halide emulsions. However, it is preferable to add them to a light-sensitive layer such as a silver halide emulsion-containing layer, a dye image providing compound-containing layer or other auxiliary layers; a subsidiary layer such as an image-receiving layer or a white reflecting layer; or a neutralizing structure such as a neutralizing layer, a neutralization timing layer or the like. Among these layers, the neutralizing layer or the neutralization timing layer is especially desirable for their addition.

In the present invention, internal latent image type silver halide emulsions can be used to advantage. Suitable examples of the emulsions of this kind include conversion type emulsions, core-shell type emulsions and emulsions with a built-in foreign metal, which are described in, e.g., U.S. Pat. Nos. 2,592,250, 3,206,313, 3,447,927, 3,761,276 and 3,935,014; and so on.

Suitable examples of a negative dye image-providing compound which is useful in the present invention include couplers capable of forming or releasing dyes by reacting with oxidized color developing agents, with specific examples including those described in U.S. Pat. No. 3,227,550, Canadian Pat. No. 602,607, and so on.

More preferable negative dye image-providing compounds are dye releasing redox compounds which can release dyes by reaction with developing agents present in an oxidized condition or with electron transfer agents. The representatives of such compounds are described in, e.g., Japanese Patent Application (OPI) Nos. 33826/73, 54021/79, 113624/76 and 71072/81, and so on. On the other hand, suitable examples of immobile, positive dye image-providing compounds which can be used in the present invention include compounds of the kind which release diffusible dyes without receiving any electron (that is, without being reduced) or after receiving at least one electron (that is, after being reduced) during the phoographic processing under an alkaline condition. Specific examples of the compounds of the above-described kind are described in Japanese Patent Application (OPI) Nos. 111628/74, 63618/76, 4819/77, 69033/78, 110827/78, 110828/78 and 130927/79.

Specific examples of yellow dye image-providing compounds which can be used in the present invention include those described in Japanese Patent Publication No. 2618/74, U.S. Pat. No. 3,309,199, Japanese Patent Publication No. 12140/82, Japanese Patent Application (OPI) Nos. 114930/76, 111344/79, 16130/81, 71072/81, 79031/79, 64036/78 and 23527/79, U.S. Pat. Nos. 4,148,641, and 4,148,643, *Research Disclosure*, No. 17630 (1978) and ibid., No. 16475 (1977).

Specific examples of magenta dye image-providing compounds which can be used in the present invention include those described in U.S. Pat. No. 3,453,107, Japanese Patent Publication No. 43950/71, Japanese Patent Application (OPI) No. 106727/77, U.S. Pat. Nos. 3,932,380, 3,931,144 and 3,932,308, Japanese Patent Application (OPI) Nos. 115528/75, 106727/77, 23628/78, 65034/79, 36804/80, 161332/79, 4028/80, 73057/81, 71060/81, 134/80 and 35533/78 and U.S. Pat. Nos. 4,207,104 and 4,287,292.

Specific examples of cyan dye image-providing compounds which can be used in the present invention include those described in Japanese Patent Publication No. 32130/73, Japanese Patent Application (OPI) Nos. 8827/77, 126331/74, 109928/76, 99431/79, 149328/78, 8827/77, 47823/78, 143323/78, 99431/79, 71061/81, 64035/78 and 121125/79, U.S. Pat. Nos. 4,142,891, 4,195,994, 4,147,544 and 4,148,642, European Pat. Nos. 53,037 and 53,040, *Research Disclosure*, No. 17630 (1978) and ibid., No. 16475 (1977).

The compounds according to the present invention can also be employed in a silver dye bleach process as described in T. H. James (editor), *The Theory of the Photographic Process*, 4th ed., chaper 12, pages 363–366 (Title: *Principles and Chemistry of Color Photography IV, Silver Dye Bleach Process*), Macmillan, New York (1977).

Moreover, the compounds according to the present invention can be employed in black and white photographic light-sensitive materials. Suitable examples of such photographic materials include Medical X-ray films for direct photographing, black and white films for general photographing, lithographic films, scanner films and so on.

Any of silver chloride, silver bromide, silver iodide, silver chlorobromide, silver chloroiodide, silver iodobromide and silver chloroiodobromide can be used for the silver halide emulsion according to the present invention.

The silver halide emulsion can include coarse silver halide grain, fine silver halide grains or mixture thereof and can be prepared by a known method, for example, a single-jet method, a double-jet method or a controlled double jet method, etc.

The silver halide grains can have an uniform structure from an outer portion to an inner portion or a layered structure in which an outer portion and an inner portion are different. They can also be the so-called conversion type emulsions as described in British Pat. No. 635,841, U.S. Pat. No. 3,622,318, etc. Further, emulsion that form latent images predominantly on the surfaces of the silver halide grains or internal latent image type emulsions that form latent images predominantly in the interior of the silver halide grains can be employed. These photographic emulsions can be prepared by various methods such as an ammonia method, a neutral method, an acidic method, etc. as well known in the art and described in C. E. K. Mees, *The Theory of the Photographic Process*, Macmillan, Glafkides, *Photographic Chemistry*, Fountain Press, *Research Disclosure*, Vol. 176, No. 17643 (December, 1978), etc.

The mean grain size of silver halide grains (which is determined by, for example, a projected area method or a number average method) is preferably from about $0.04\mu$ to $4\mu$ and particularly $0.7\mu$ or less.

During the formation of silver halide grains, ammonia, potassium thiocyanate, ammonium thiocyanate, a thioether compound (for example, U.S. Pat. Nos. 3,271,157, 3,574,628, 3,704,130, 4,297,439 and 4,276,374, etc.), a thione compound (for example, Japanese Patent Application (OPI) Nos. 144319/78, 82408/78 and 77737/80, etc.), an amine compound (for example, Japanese Patent Application (OPI) No. 100717/79, etc.) and so on can be employed as a silver halide solvent in order to control the growth of silver halide grains.

Further, a water-soluble rhodium salt and/or a water-soluble iridium salt may be added before, during or after the formation of silver halide grains.

To the silver halide photographic emulsions, conventionally used chemical sensitization, for example, gold sensitization (as described in U.S. Pat. Nos. 2,540,085, 2,597,876, 2,597,915, 2,399,083, etc.), sensitization with a metal ion of Group VIII of the Periodic Table (as described in U.S. Pat. Nos. 2,448,060, 2,540,086, 2,566,245, 2,566,263 and 2,598,079, etc.), sulfur sensitization (as described in U.S. Pat. Nos. 1,574,944, 2,278,947, 2,440,206, 2,521,926, 3,021,215, 3,038,805, 2,410,689, 3,189,458, 3,415,649 and 3,635,717, etc.), reduction sensitization (as described in U.S. Pat. Nos. 2,518,698, 2,419,974 and 2,983,610, *Research Disclosure*, Vol. 176, No. 17643, III (December, 1978), etc.), sensitization with a thioether compound (as described in U.S. Pat. Nos. 2,521,926, 3,021,215, 3,038,805, 3,046,129, 3,046,132, 3,046,133, 3,046,134, 3,046,135, 3,057,724, 3,062,646, 3,165,552, 3,189,458, 3,192,046, 3,506,443, 3,671,260, 3,574,709, 3,625,697, 3,635,717 and 4,198,240, etc.), or a combination thereof can be applied.

Specific examples of the chemical sensitizers include a sulfur sensitizer, for example, allylthiocarbamide, thiourea, sodium thiosulfate, thioether, cystine, etc.; a noble metal sensitizer, for example, potassium chloroaurate, aurous thiosulfate, potassium chloropalladate, etc.; a reduction sensitizer, for example, stannous chloride, phenylhydrazine, reductone, etc.

Moreover, the photographic emulsions may contain a sensitizer, for example, a polyoxyethylene derivative (as described in British Pat. No. 981,470, Japanese Patent Publication No. 6475/66, U.S. Pat. No. 2,716,062, etc.), a polyoxypropylene derivative, a derivative having a quaternary ammonium group, etc.

For the purpose of preventing the reduction of sensitivity and the occurrence of fog during the production, the storage or the photographic processing of the photographic light-sensitive materials, various compounds can be added to the photographic emulsions used in the present invention. As such compounds a large number of compounds are known, for example, nitrobenzimidazole, ammonium chloroplatinate, 4-hydroxy-6-methyl-1,3,3a,7-tetraazaindene, 3-methylbenzothiazole, 1-phenyl-5-mercaptotetrazole and many other heterocyclic compounds, mercury containing compounds, mercapto compounds and metal salts. Examples of compounds which can be used are described in C. E. K, Mees, *The Theory of the Photographic Process*, 3rd Ed., pages 344–349 (1966). Further, examples of these compounds include thiazolium salts as described in U.S. Pat. Nos. 2,131,038 and 2,694,716, etc.; azaindenes as described in U.S. Pat. Nos. 2,886,437 and 2,444,605, etc.; urazoles as described in U.S. Pat. No. 3,287,135, etc.; sulfocatechols as described in U.S. Pat. No. 3,236,652, etc.; oximes as described in British Pat. No. 623,448, etc.; mercaptotetrazoles as described in U.S. Pat. Nos. 2,403,927, 3,266,897 and 3,397,987, etc.; nitron; nitroindazoles; polyvalent metal salts as described in U.S. Pat. No. 2,839,405, etc.; thiuronium salts as described in U.S. Pat. No. 3,220,839, etc.; palladium, platinum or gold salts as described in U.S. Pat. Nos. 2,566,263 and 2,597,915, etc.; and so on.

The photographic emulsions used in the present invention can be spectrally sensitized with dyes. Useful examples of the sensitizing dyes are described in, for example, U.S. Pat. Nos. 3,703,377, 2,688,545, 3,397,060, 3,615,635 and 3,628,964, British Pat. Nos. 1,242,588 and 1,293,862, Japanese Patent Publication Nos. 4936/68, 14030/69 and 10773/68, U.S. Pat. No. 3,416,927, Japanese Patent Publication No. 4930/68, U.S. Pat. Nos. 3,615,613, 3,615,632, 3,617,295 and 3,635,721, etc. Further, these sensitizing dyes can be used in combination, if desired.

Hardening of the photographic emulsions are carried out in a conventional manner. Useful examples of hardeners include, for example, aldehyde type compounds such as formaldehyde, glutaraldehyde, etc.; ketone compounds such as diacetyl, cyclopentadione, etc.; active halogen compounds such as bis(2-chloroethylurea), 2-hydroxy-4,6-dichloro-1,3,5-triazine, the compounds as described in U.S. Pat. Nos. 3,288,775 and 2,732,303, British Pat. Nos. 974,723 and 1,167,207, etc.; active olefin compounds such as divinylsulfone, 5-acetyl-1,3-diacryloylhexahydro-1,3,5-triazine, the compounds as described in U.S. Pat. Nos. 3,635,718 and 3,232,763, British Pat. No. 994,869, etc.; N-methylol compounds such as N-hydroxymethylphthalimide, the compounds as described in U.S. Pat. Nos. 2,732,316 and 2,586,168, etc.; isocyanates such as the compounds as described in U.S. Pat. No. 3,103,437, etc.; aziridine compounds such as the compounds as described in U.S. Pat. Nos. 3,017,280 and 2,983,611, etc.; acid derivatives such as the compounds as described in U.S. Pat. Nos. 2,725,294 and 2,725,295, etc.; carbodiimide type compounds such as the compounds as described in U.S. Pat. No. 3,100,704, etc.; epoxy compounds such as the compounds as described in U.S. Pat. No. 3,091,537, etc.; isooxazole type compounds such as the compounds as described in U.S. Pat. Nos. 3,321,313 and 3,543,292, etc.; halogeno carboxyaldehydes such as mucochloric acid, etc.; dioxane derivatives such as dihydroxydioxane, dichlorodioxane, etc.; inorganic hardeners such as chromium alum, zirconium sulfate, etc., and so on. Also, precursors of hardeners can be used. For example, alkali metal bisulfite aldehyde adducts, methylol derivatives of hydantoin, primary aliphatic nitroalcohols, etc. can be used.

To the photographic emulsions used in the present invention can be added surface active agents, alone or in combination. They are utilized as coating aids or for various purposes, such as emulsification and dispersion, sensitization, improvement in photographic properties, prevention of charging, prevention of adhesion, etc. Examples of useful surface active agents include natural surface active agents such as saponin, etc.; nonionic surface active agents such as alkylene oxide derivatives, glycerol derivatives, glycidol derivatives, etc.; cationic surface active agents such as higher alkyl amines, quaternary ammonium salts, pyridine and other heterocyclic compounds, phosphoniums, sulfoniums, etc.; anionic surface active agents containing an acidic group such as a carboxylic acid group, a sulfonic acid group, a phosphoric acid group, a sulfate group, a phosphate group, etc.; amphoteric surface active agents such as amino acids, aminosulfonic acids, sulfates or phosphates of aminoalcohols.

Examples of useful surface active agents are described in U.S. Pat. Nos. 2,271,623, 2,240,472, 2,288,226, 2,739,891, 3,068,101, 3,158,484, 3,201,253, 3,210,191, 3,294,540, 3,415,649, 3,441,413, 3,442,654, 3,475,174 and 3,545,974, German Pat. (OLS) No. 1,942,665, British Pat. Nos. 1,077,317 and 1,198,450, Ryohei Oda, *Synthesis of Surfactants and their Applications,* Maki Shoten, (1964), A. W. Perry, *Surface Active Agents,* Interscience Publication Inc., (1958), J. P. Sisley, *Encyclopedia of Surface Active Agents,* Vol. 2, Chemical Publishing Co., (1964), etc.

Examples of polyalkyleneoxide compounds to be employed in the present invention include products obtained by the condensation reaction of polyalkyleneoxides having at least 10 units of alkyleneoxide containing from 2 to 4 carbon atoms, for example, ethylene oxide, propylene-1,2-oxide, butylene-1,2-oxide, etc., especially ethylene oxide, with compounds containing at least one active hydrogen atom, for example, water, aliphatic alcohols, aromatic alcohols, fatty acids, organic amines, hexitol derivatives, etc.; and block copolymers of two or more kinds of polyalkyleneoxides. More specifically, polyalkylene glycols, polyalkylene glycol alkyl ethers, polyalkylene glycol aryl ethers, polyalkylene glycol (alkyl aryl) esters, polyalkylene glycol esters, polyalkylene glycol fatty acid amides, polyalkylene glycol amines, polyalkylene glycol block copolymers, polyalkylene glycol grafted polymers and so on can be used as such polyalkyleneoxide compounds. Molecular weight of the polyalkyleneoxide compounds is at least 600.

Two or more polyalkylene oxide chains may be contained in the molecule. In this case, each polyalkylene oxide chain may be composed of less than 10 alkylene oxide units, but the total alkylene oxide units in the molecule should be at least 10. Where two or more polyalkylene oxide chains are contained in the molecule, they may be composed of different alkylene oxide units, for example, ethylene oxide and propylene oxide. Preferred polyalkylene oxide compounds as used in the present invention are those containing from 14 to 100 of alkylene oxide units.

Specific examples of the polyalkyleneoxide compounds which can be used in the present invention are set forth below.

| | |
|---|---|
| HO(CH₂CH₂O)₉₀H | P-1 |
| C₄H₉O(CH₂CH₂O)₁₅H | P-2 |
| C₁₂H₂₅O(CH₂CH₂O)₁₅H | P-3 |
| C₁₈H₃₇O(CH₂CH₂O)₁₅H | P-4 |
| C₁₈H₃₇O(CH₂CH₂O)₄₀H | P-5 |
| C₈H₁₇CH=CHC₈H₁₆O(CH₂CH₂O)₁₅H | P-6 |

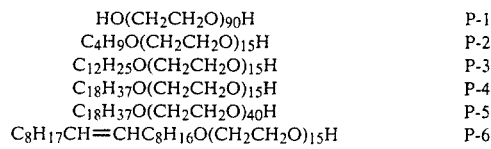
P-7

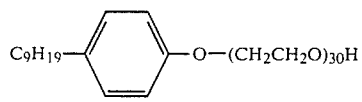
P-8

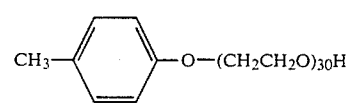
P-9

| | |
|---|---|
| C₁₁H₂₃COO(CH₂CH₂O)₈₀H | P-10 |
| C₁₁H₂₃COO(CH₂CH₂O)₂₄OCC₁₁H₂₃ | P-11 |

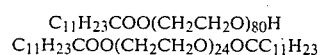
P-12

| | |
|---|---|
| C₁₁H₂₃CONH(CH₂CH₂O)₁₅H | P-13 |

P-14

| | |
|---|---|
| C₁₄H₂₉N(CH₃)(CH₂CH₂O)₂₄H | P-15 |

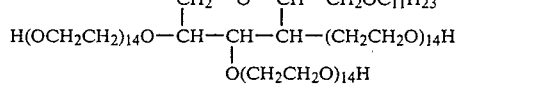
P-16

P-17
a + b + c = 50
b:a + c = 10:9

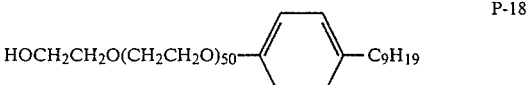
P-18

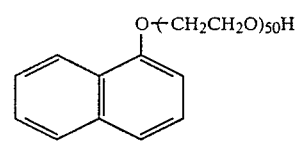
P-19

HO(CH₂CH₂O)ₐ(CH₂CH₂CH₂CH₂O)ᵦ(CH₂CH₂O)cH    P-20
a + c = 30, b = 14

HO(CH₂CH₂O)ₐ(CHCH₂O)ᵦ(CH₂CH₂O)cH    P-21

b = 8, a + c = 50

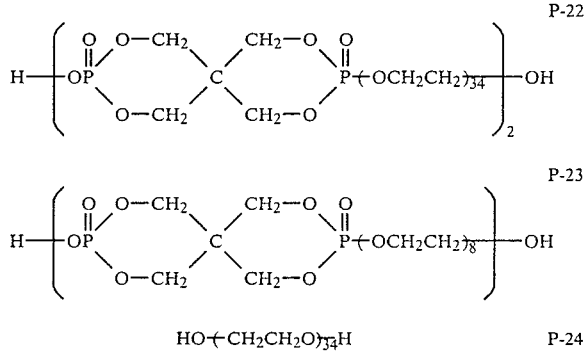

HO—(CH₂CH₂O)₃₃H  P-24

The polyalkylene oxide compounds illustrated above are described in Japanese Patent Application (OPI) Nos. 156423/75, 108130/77 and 3217/78. These polyalkylene oxide compounds may be used alone or in mixture two or more thereof.

When the polyalkylene oxide compounds are added to the silver halide emulsion, they can be added as a suitable concentration of an aqueous solution or after being dissolved in an organic solvent having a low boiling point which is compatible with water, at an appropriate stage prior to the coating thereof, preferably after the chemical ripening thereof. The polyalkylene oxide compounds are preferably used in an amount ranging from $1\times 10^{-5}$ mol to $1\times 10^{-2}$ mol.

The silver halide photographic emulsions used in the present invention can contain as protective colloids gelatin; acylated gelatin such as phthalated gelatin, malonated gelatin, etc.; cellulose compounds such as hydroxyethylcellulose, carboxymethylceullulose, etc.; soluble starch such as dextrin, etc.; hydrophilic polymers such as polyvinylalcohol, polyvinylpyrrolidone, polyacrylamide, polystyrenesulfonic acid, etc.

Further, the photographic emulsions used in the present invention may contain polymer latexes composed of homopolymers or copolymers or alkyl acrylates, alkyl methacrylates, acrylic acid, glycidyl acrylate, etc. as described in U.S. Pat. Nos. 3,411,911, 3,411,912, 3,142,568, 3,325,286 and 3,547,650, Japanese Patent Publication No. 5331/70, etc. for the purpose of improvement in dimensional stability or film properties, etc.

The silver halide photographic emulsions used in the present invention can contain developing agents, for example, hydroquinones, catechols, aminophenols, 3-pyrazolidones, ascorbic acid and derivatives thereof, reductones, phenylenediamines, or mixture thereof. The developing agents may be incorporated into the silver halide emulsion layer and/or other photographic layers (for example, a protective layer, an intermediate layer, a filter layer, an antihalation layer, a back layer, etc.). The developing agents can be added by dissolving in an appropriate solvent or in the form of dispersions as described in U.S. Pat. No. 2,592,368, French Pat. No. 1,505,778, etc.

As development accelerators, compounds as described, for example, in U.S. Pat. Nos. 3,288,612, 3,333,959, 3,345,175 and 3,708,303, British Pat. No. 1,098,748, West German Pat. Nos. 1,141,531 and 1,183,784, etc. can be used.

The silver halide photographic emulsions may further contain antistatic agents, plasticizers, fluorescent whitening agents, aero-fog preventing agents, toning agents.

Moreover, the photographic emulsion may contain irradiation preventing dyes depending on purpose. Examples of useful dyes are described, for example, in Japanese Patent Publication Nos. 20389/66, 3504/68 and 13168/68, U.S. Pat. Nos. 2,697,037, 3,423,207 and 2,865,752, British Pat. Nos. 1,030,392 and 1,100,546, etc.

The exposure for obtaining a photographic image in the present invention may be carried out in a conventional manner. Any various known light sources including infrared rays can be employed for the exposure. Examples of useful light sources include natural light (day light), a tungsten lamp, a fluorescent lamp, a mercury lamp, a xenon arc lamp, a carbon arc lamp, a xenon flash lamp, cathode-ray tube flying spot, a light-emitting diode, a laser beam (for example, gas laser, YAG laser, dye laser, semiconductor laser, etc.), and so on. Further light generated from a phosphor which is excited by an electron beam, an X-ray, a γ-ray or an α-ray, etc. can be employed for the exposure. Suitable exposure times which can be used include not only exposure times commonly used in cameras ranging from 1/1000 to 1 sec., but also exposure times shorter than 1/1000 sec., for example, about $1/10^4$ to about $1/10^6$ sec. as used with xenon flash lamps and cathode-ray tubes. Exposure times longer than 1 second can also be used. The spectral distribution of the light employed for the exposure can be controlled using color filters, if desired.

There are no particular restrictions with respect to development processing of the silver halide photographic light-sensitive materials of the present invention. Known methods and processing solutions, for example, those are described in *Research Disclosure*, Vol. 176, No. 17643, pages 28 to 30 can be utilized in the present invention. The photographic processing may be either the photographic processing for forming silver images (black and white photographic processing) or that for forming dye images (color photographic processing), if desired. A processing temperature is usually selected from the range of 18° C. to 50° C. Of course, temperatures lower than 18° C. or those higher than 50° C. may be employed.

Developing solutions to be employed for black and white photographic processing can contain known developing agents. Suitable examples of developing agents include dihydroxybenzenes (e.g., hydroquinone), 3-pyrazolidones (e.g., 1-phenyl-3-pyrazolidone), aminophenols (e.g., N-methyl-p-aminophenol) and so on. These developing agents may be employed independently or in combination of two or more thereof. In addition to the developing agent, a developing solution may generally contain known a preservative, an alkali agent, a pH buffer and an antifoggant and optionally, a dissolution aid, a color toning agent, a development accelerator, a surface active agent, a defoaming agent, a water softener, a hardener, a viscosity providing agent and so on.

To the photographic emulsion of the present invention, the so-called "lithographic type" of development processing can be applied. "Lithographic type" of development processing is the processing in which in order to effect the photographic reproduction of line images or the photographic reproduction of halftone images by means of dots, dihydroxybenzenes are generally used as a developing agent and the development step is made to proceed infectiously under the condition that the concentration of sulfite ion is maintained at a low level (the details of which are described in L. F. A. Mason, *Photographic Processing Chemistry*, pages 163 to 165, Focal Press (1966)).

To the case of forming dye images, conventional methods can be applied. For instance, a nega-posi process (as described in *Journal of the Society of Molten Picture and Television Engineers*, Vol. 61, pages 667 to 701 (1953)); a color reversal process which comprises forming negative silver images by development with a developing solution containing a black and white developing agent, subjecting the photographic material to uniform exposure at least once or to another proper fogging treatment and subsequently, carrying out color development to produce positive dye images; a silver dye bleach process which comprises exposing dye-containing photographic emulsions to light, developing the emulsions to produce silver images, and bleaching the dyes using the silver images as a bleaching catalyst; and so on can be employed.

A color developing solution is, in general, an alkaline aqueous solution containing a color developing agent. Suitable examples of color developing agents which can be used include known primary aromatic amine developing agents, such as phenylenediamines (e.g., 4-amino-N,N-diethylaniline, 3-methyl-4-amino-N,N-diethylaniline, 4-amino-N-ethyl-N-$\beta$-hydroxyethylaniline, 3-methyl-4-amino-N-ethyl-N-$\beta$-hydroxyethylaniline, 3-methyl-4-amino-N-ethyl-N-$\beta$-methanesulfonamidoethylaniline, 4-amino-3-methyl-N-ethyl-N-$\beta$-methoxyethylaniline, etc.).

In addition to the above-described compounds, those described in L. F. A. Mason, *Photographic Processing Chemistry*, pages 226 to 229, Focal Press (1966), U.S. Pat. Nos. 2,193,015 and 2,592,364, and Japanese Patent Application (OPI) No. 64933/73, etc. can be also used as a color developing agent.

After the color development processing, photographic emulsion layers are generally subjected to bleach processing. The bleach processing may be carried out simultaneously with fix processing, or separately therefrom. Suitable examples of bleaching agents include compounds of polyvalent metals such as iron (III), cobalt (IV), chromium (IV), copper (II), etc. peroxy acids, quinones, nitroso compounds, and so on.

Now, the present invention will be illustrated in more detail with reference to the following examples, but the present invention should not be construed as being limited thereto.

EXAMPLE 1

In order to evaluate the effectiveness of the anti-foggant precursors according to the present invention, and the comparison compounds corresponding thereto, samples A to I were prepared as follows: One of the antifoggant precursors (blocked photographic agents) according to the present invention or one of antifoggants corresponding thereto, respectively (for comparison), which are set forth in Table 1 below, was dissolved in tricresyl phosphate together with the coupler (Cp-1), emulsified and added to a silver halide emulsion. The resulting emulsion was coated on a cellulose triacetate support having a subbing layer. The coated amount of each component was expressed in terms of g/m$^2$ or mol/m$^2$ and designated in parentheses.

(1) Emulsion Layer
  Negative type silver iodobromide emulsion having a grain size of 1.4$\mu$ (silver: $1.6 \times 10^{-2}$ mol/m$^2$)
  Magenta Coupler Cp-1
  ($1.33 \times 10^{-3}$ mol/m$^2$)
  Antifoggant or antifoggant precursor according to the present invention (as shown in Table 1)
  Gelatin
  (2.50 g/m$^2$)
(2) Protective Layer
  Gelatin
  (1.30 g/m$^2$)
  Sodium 2,4-dichloro-6-hydroxy-s-triazine
  (0.05 g/m$^2$)

These films were allowed to stand for 14 hours under the conditions of 40° C. and relative humidity of 70%. Thereafter, they were subjected to imagewise exposure for sensitometry and then, to the following color development processing.

| Steps for Color Development Processing | Time | Temperature |
|---|---|---|
| 1. Color Development | 3'15" | 38° C. |
| 2. Bleaching | 6'30" | " |
| 3. Water washing | 2' | " |
| 4. Fixing | 4' | " |
| 5. Water washing | 4' | " |
| 6. Stabilizing | 1' | " |

Compositions of the processing solutions employed in the above-described steps are described below.

| Color Developing Solution: | |
|---|---|
| Water | 800 ml |
| 4-(N—ethyl-N—hydroxyethyl)amino-2-methylaniline sulfate | 5 g |
| Sodium Sulfite | 5 g |
| Hydroxylamine Sulfate | 2 g |
| Potassium Carbonate | 30 g |
| Potassium Hydrogencarbonate | 1.2 g |
| Potassium Bromide | 1.2 g |
| Sodium Chloride | 0.2 g |
| Trisodium Nitrilotriacetate | 1.2 g |
| Water to make | 1 liter |
| | (pH = 10.1) |

| Bleaching Solution: | |
|---|---|
| Water | 800 ml |
| Ammonium Ferric Ethylenediaminetetraacetate | 100 g |
| Disodium Ethylenediaminetetraacetate | 10 g |
| Potassium Bromide | 150 g |
| Acetic Acid | 10 g |
| Water to make | 1 liter |
| | (pH = 6.0) |

| Fixing Solution: | |
|---|---|
| Water | 800 ml |
| Ammonium Thiosulfate | 150 g |
| Sodium Sulfite | 10 g |
| Sodium Hydrogensulfite | 2.5 g |
| Water to make | 1 liter |
| | (pH = 6.0) |

| Stabilizing Solution: | |
|---|---|
| Water | 800 ml |
| Formaline (37%) | 5 ml |
| Driwel | 3 ml |
| Water to make | 1 liter |

The photographic properties thus-obtained are shown in Table 1 below.

TABLE 1

| Sample | Precursor Compound of the Present Invention or Comparison Antifoggants | Amount Added (mol/m²) | Fog | Gamma | Relative* Sensitivity | Maximum Color Density |
|---|---|---|---|---|---|---|
| A (Control) | none | — | 0.12 | 0.82 | 100 | 1.60 |
| B (Invention) | (11)** | $1.1 \times 10^{-5}$ | 0.07 | 0.78 | 95 | 1.52 |
| C (Invention) | (1)** | $1.1 \times 10^{-5}$ | 0.07 | 0.77 | 92 | 1.48 |
| D (Invention) | (8)*** | $2.2 \times 10^{-5}$ | 0.08 | 0.79 | 98 | 1.57 |
| E (Invention) | (16)**** | $1.1 \times 10^{-4}$ | 0.09 | 0.82 | 100 | 1.60 |
| F (Comparison) | A-1 | $2.2 \times 10^{-6}$ | 0.05 | 0.40 | 26 | 0.93 |
| G (Comparison) | A-2 | $4.4 \times 10^{-6}$ | 0.03 | 0.51 | 33 | 1.08 |
| H (Comparison) | A-3 | $2.2 \times 10^{-5}$ | 0.08 | 0.64 | 52 | 1.35 |
| I (Comparison) | A-4 | $1.1 \times 10^{-5}$ | 0.07 | 0.70 | 75 | 1.25 |

*Relative sensitivity is shown by a reciprocal of an exposure amount required for obtaining a color density of fog + 0.2 and with the sensitivity of Control Sample 1 as 100.
**Compounds (11) and (1) are the precursors in which Antifoggant A-1 is blocked by the technique according to the present invention.
***Compound (8) is the precursor in which Antifoggant A-2 is blocked by the technique according to the present invention.
****Compound (16) is the precursor in which Antifogant A-3 is blocked by the technique according to the present invention.

The coupler and the antiffogants for comparison employed in the above-described samples are illustrated below.

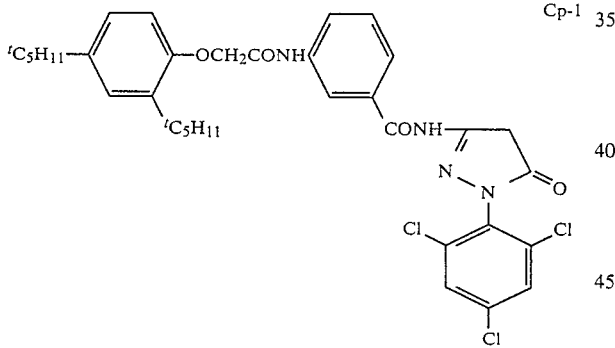

Cp-1

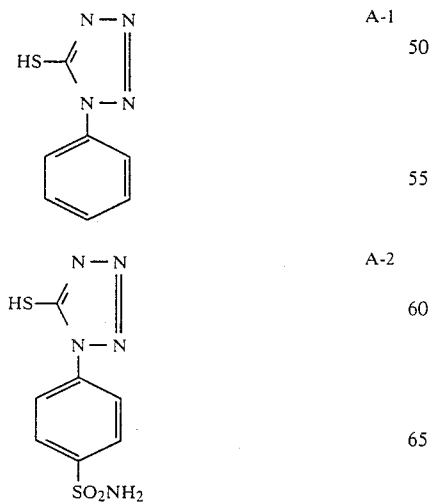

A-1

A-2

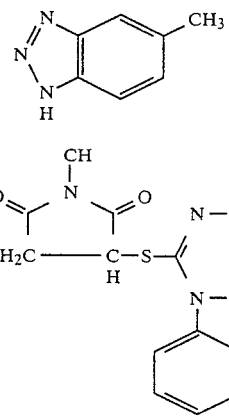

A-3

A-4

(precursor described in U.S. Pat. No. 3,888,677)

It is apparent from the results shown in Table 1 above that in Samples B to E which contain the blocked antiffogants according to the present invention, the occurrence of fog is depressed without hardly accompanying a decrease in gamma, sensitivity and maximum color density.

EXAMPLE 2

Sample B (present invention) and Sample I (containing the precursor for comparison) as described in Example 1 were stored for 1 week under the conditions of 40° C. and relative humidity of 80% and then subjected to the imagewise exposure and development processing in the same manner as Example 1. As the result it was found that Sample I showed the remakably low values of gamma, sensitivity and maximum color density in comparison with Sample B. From these results it is understood that the precursor according to the present invention has a good storage stability while the precursor used in Sample I lacks good stability since the blocking moiety thereof has the tendency of leaving during storage.

EXAMPLE 3

To an aqueous solution containing 70 g of gelatin were simultaneously added at a constant rate an aqueous solution containing 1 kg of silver nitrate and an aqueous solution containing 210 g of potassium bromide and 200 g of sodium chloride over a period of 30 minutes. After removing the soluble salts, gelatin was added to the emulsion which was then subjected to gold sensitization and sulfur sensitization to obtain a silver chlorobromide emulsion (grain size: 0.27μ, bromide content: 30 mol%). To the emulsion were added in order 4-hydroxy-6-methyl-1, 3,3a,7-tetraazaindene as a stabilizer, the blocked photographic agent (precursor) according to the present invention as shown in Table 2 below, sodium 2-hydroxy-4,6-dichloro-s-triazine as a hardener and sodium dodecylbenzenesulfonate as a coating aid, and the resulting coating solution was applied to a polyethylene terephthalate film at a silver coated amount of 4.2 g/m².

The film samples thus-prepared were exposed to light with a wedge using xenon flash lamp for $10^{-5}$ sec. and developed with the developing solution shown below at 27° C. for 4 minutes followed by stopping, fixing, water washing and drying. The densities of the thus-processed films were measured using a P-type densitometer (manufactured by Fuji Photo Film Co., Ltd.) and the sensitivity and fog value were obtained. The standard point of optical density for determing the sensitivity was a point of fog +0.5. The results thus obtained are shown in Table 2 below.

| Composition of the developing solution | |
|---|---|
| Metol | 0.31 g |
| Anhydrous Sodium Sulfite | 39.6 g |
| Hydroquinone | 6.0 g |
| Anhydrous Sodium Carbonate | 18.7 g |
| Potassium Bromide | 0.86 g |
| Citric Acid | 0.68 g |
| Potassium Methahydrogen Sulfite | 1.5 g |
| Water to make | 1 liter |

TABLE 2

| No. | Precursor | Amount Added (mol/Kg emulsion) | Fog | Sensitivity |
|---|---|---|---|---|
| 1 (Control) | none | — | 0.07 | 100 (Standard) |
| 2 (Invention) | (1) | $3 \times 10^{-4}$ | 0.04 | 88 |
| 3 (Invention) | (7) | $3 \times 10^{-4}$ | 0.04 | 89 |
| 4 (Invention) | (9) | $3 \times 10^{-4}$ | 0.04 | 88 |
| 5 (Invention) | (11) | $3 \times 10^{-4}$ | 0.04 | 96 |
| 6 (Invention) | (12) | $3 \times 10^{-4}$ | 0.05 | 93 |
| 7 (Invention) | (13) | $3 \times 10^{-4}$ | 0.05 | 98 |
| 8 (Invention) | (15) | $3 \times 10^{-4}$ | 0.05 | 95 |
| 9 (Comparison) | A - 1 | $3 \times 10^{-4}$ | 0.05 | 48 |

Comparison Compound A-1

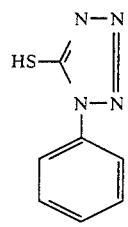

From the results shown in Table 2 above it is apparent that the compounds according to the present invention can depress the fog accompanying with a very slight decrease in the sensitivity in comparison with Comparison Compound A-1.

EXAMPLE 4

A silver halide emulsion containing 80 mol% of silver chloride, 19.5 mol% of silver bromide and 0.5 mol% of silver iodide was subjected to gold sensitization and sulfur sensitization. The mean grain size of silver halide grains in the emulsion was 0.31μ.

To each 1 kg of the silver halide emulsion were added the blocked photographic agent according to the present invention as shown in Table 3 below, 0.1 g of 3-carboxymethyl-5-(3-ethyl-2-thiazolidinylidenethylidene)-rhodanine (spectral sensitizer), 0.18 g of 4-hydroxy-6-methyl-1,3,3a,7-tetraazaindene (stabilizer), 0.45 g of polyalkylene oxide compound (P-21), 1.2 g of sodium dodecylbenzenesulfonate (surface active agent), 0.48 g of mucochloric acid (hardener) and 30 g of a polymer latex as described in Japanese Patent Publication No. 5331/70, and the resulting coating solution was applied to a polyethylene terephthalate film at a silver coated amount of 3.9 g/m² to prepare a photographic light-sensitive material.

The samples thus-prepared were contacted with a gray contact screen for negative (150 L/inch, manufactured by Dai-nippon Screen Co., Ltd.) and exposed to tungsten light (color temperature of 5400° K.) for 1 second through a step wedge having a difference of 0.1 (log E) in each step. Then samples were developed at 27° C. for 100 seconds using an automatic developing machine with the lith type developing solution shown below, stopped, fixed, washed with water and dried.

| Composition of the developing solution | |
|---|---|
| Hydroquinone | 15 g |
| Formaldehyde Sodium Hydrogen Sulfite Adduct | 50 g |
| Potassium Carbonate | 30 g |
| Sodium Sulfite | 2.5 g |
| Potassium Bromide | 2.0 g |
| Boric Acid | 5.0 g |
| Sodium Hydroxide | 3.0 g |
| Triethylene glycol | 40 g |
| Disodium Ethylenediaminetetraacetate | 1.0 g |
| Water to make | 1000 ml |

The samples thus-processed were measured with dot areas of 10%, 50% and 90% respectively and the sensitivity of the samples were compared by a reciprocal of an exposure amount required for obtaining the dot area of 50%. Further, the screen range was determined from the difference between the logarithm of an exposure amount providing a dot area of 10% and that of an exposure amount providing a dot area of 90%. The results thus-obtained are shown in Table 3 below.

TABLE 3

| No. | Precursor | Amount Added (mol/Kg emulsion) | Sensitivity | Fog | Screen Range |
|---|---|---|---|---|---|
| 1 (Control) | none | — | 100 (Standard) | 0.06 | 0.9 |
| 2 (Invention) | (2) | $2 \times 10^{-4}$ | 98 | 0.04 | 1.0 |
| 3 (Invention) | (2) | $4 \times 10^{-4}$ | 95 | 0.04 | 1.1 |
| 4 (Comparison) | A-5 | $2 \times 10^{-4}$ | 54 | 0.04 | 1.0 |
| 5 (Comparison) | A-5 | $4 \times 10^{-4}$ | 42 | 0.04 | 1.1 |
| 6 (Invention) | (10) | $2 \times 10^{-4}$ | 100 | 0.04 | 1.1 |
| 7 (Invention) | (10) | $4 \times 10^{-4}$ | 95 | 0.04 | 1.2 |
| 8 (Comparison) | A-1 | $2 \times 10^{-4}$ | 49 | 0.04 | 1.1 |
| 9 (Comparison) | A-1 | $4 \times 10^{-4}$ | 39 | 0.04 | 1.1 |

Comparison Compound A-5

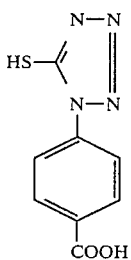

From the results shown in Table 3 above it is apparent that the compounds according to the present invention can depress the fog without substantial decrease in the sensitivity. Further, the compounds according to the present invention can obtain an improved screen range without substantial decrease in the sensitivity.

While the invention has been described in detail and with reference to specific embodiments thereof, it will be apparent to one skilled in the art that various changes and modifications can be made therein without departing from the spirit and scope thereof.

What is claimed is:

1. A silver halide photographic light-sensitive material which comprises a support having thereon a light-sensitive silver halide emulsion layer, wherein the photographic light sensitive material therein contains a blocked photographic agent represented by the formula (I):

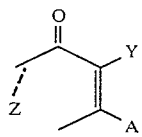

wherein A represents a photographic agent moiety which is bonded to a blocking moiety through a hetero atom or a group which is bonded to a blocking moiety through a hetero atom and capable of releasing a photographic agent upon a subsequent reaction after the group is released; Y represents a hydrogen atom or a substituent; and Z represents an atomic group necessary to form a carbocyclic ring or a heterocyclic ring.

2. A silver halide photographic light-sensitive material as claimed in claim 1, wherein the blocked photographic agent is represented by formula (I')

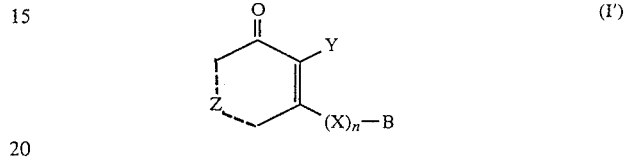

wherein B represents a photographic agent moiety which is bonded to a blocking moiety through a hetero atom; X represents a divalent linking group; n represents 0 or 1; Y represents a hydrogen atom or a substituent; and Z represents an atomic group necessary to form a carbocyclic ring or a heterocyclic ring.

3. A silver halide photographic light-sensitive material as claimed in claim 2, wherein the substituent represented by Y is selected from the group consisting of a hydrogen atom, a halogen atom, an alkyl group, an alkenyl group, an aryl group, an alkoxy group, an aryloxy group, an acyloxy group, a carbonic acid ester group, an amino group, a carbonamido group, a ureido group, a carboxy group, an oxycarbonyl group, a carbamoyl group, an acyl group, a sulfo group, a sulfonyl group, a sulfamoyl group, a cyano group and a nitro group.

4. A silver halide photographic light-sensitive material as claimed in claim 2, wherein the photographic agent in the moiety represented by B is selected from the group consisting of an antifoggant, a development restrainer, a developing agent, an auxiliary developing agent, a fogging agent, a silver halide solvent, a bleach accelerating agent and a dye.

5. A silver halide photographic light-sensitive material as claimed in claim 4, wherein the photographic agent is selected from the group consisting of mercaptotetrazoles, mercaptotriazoles, mercaptopyrimidines, mercaptobenzimidazoles, mercaptoimidazoles, mercaptothiadiazoles, benzotriazoles and indazoles.

6. A silver halide photographic light-sensitive material as claimed in claim 4, wherein the photographic agent is selected from the group consisting of p-phenylenediamines, hydroquinones and p-aminophenols.

7. A silver halide photographic light-sensitive material as claimed in claim 4, wherein the photographic agent is selected from pyrazolidones.

8. A silver halide photographic light-sensitive material as claimed in claim 4, wherein the photographic agent is selected from the group consisting of hydrazines and hydrazides.

9. A silver halide photographic light-sensitive material as claimed in claim 4, wherein the photographic agent is selected from the group consisting of azo dyes and azomethine dyes.

10. A silver halide photographic light-sensitive material as claimed in claim 2, wherein the photographic agent in the moiety represented by B is a coloring material for color diffusion transfer photographic material or a development inhibitor releasing hydroquinone.

11. A silver halide photographic light-sensitive material as claimed in claim 2, wherein the photographic agent moiety represented by B is directly bonded to the blocking moiety through a hetero atom contained therein.

12. A silver halide photographic light-sensitive material as claimed in claim 2, wherein the photographic agent moiety represented by B is bonded to the divalent linking group represented by X through a hetero atom contained therein.

13. A silver halide photographic light-sensitive material as claimed in claim 2, wherein the divalent linking group represented by X is a group which releases the photographic agent by an intramolecular ring-closing reaction, a group which releases the photographic agent through intramolecular electron transfer, a group which releases the photographic agent with the evolution of carbon dioxide or a group which releases the photographic agent with the evolution of formaldehyde.

14. A silver halide photographic light-sensitive material as claimed in claim 12, wherein X is a group represented by the following formula

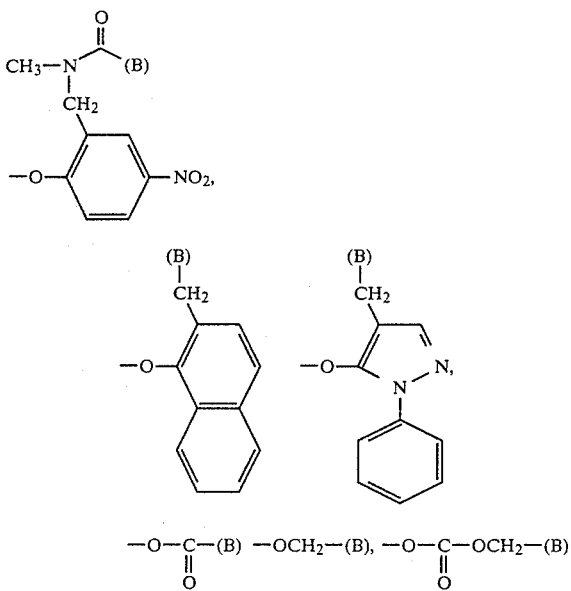

wherein —(B) represents a bond to the photographic agent moiety.

15. A silver halide photographic light-sensitive material as claimed in claim 2, wherein the ring formed with Z is a 5-membered, 6-membered or 7-membered carbocyclic ring, a 5-membered, 6-membered or 7-membered heterocyclic ring containing one or more nitrogen atoms, oxygen atoms or sulfur atoms or a condensed ring thereof.

16. A silver halide photographic light-sensitive material as claimed in claim 15, wherein the ring formed with Z is cyclopentenone, cyclohexenone, cycloheptenone, benzocycloheptenone, 4-pyridone, 4-quinolone, 2-pyrone, 4-pyrone, 1-thio-2-pyrone, 1-thio-4-pyrone, coumarin, chromone or uracil.

17. A silver halide photographic light-sensitive material as claimed in claim 15, wherein the carbocyclic ring or heterocyclic ring may be substituted with one or more substituents selected from the group consisting of a halogen atom, an alkyl group, an aryl group, an alkoxy group, an aryloxy group, an acyl group, an acylamino group, a nitro group, a cyano group, an oxycarbonyl group, a hydroxy group, a carboxy group, a sulfo group, a ureido group, a sulfonamido group, a sulfamoyl group, a carbamoyl group, an acyloxy group, an amino group, a carbonic acid ester group and a sulfone group.

18. A silver halide photographic light-sensitive material as claimed in claim 2, wherein the blocked photographic agent is represented by formula (III) or (IV):

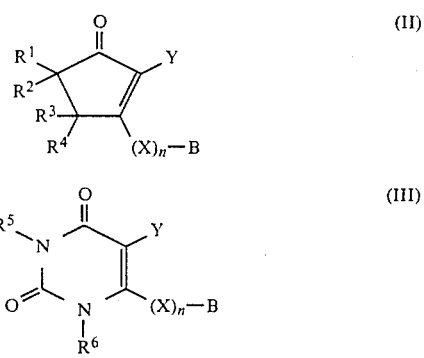

wherein B, X, Y and n each has the same meaning as defined in claim 2, and $R^1$, $R^2$, $R^3$, $R^4$, $R^5$ and $R^6$ each represents a member of the group consisting of a hydrogen atom, a halogen atom, an alkyl group, an aryl group, an alkoxy group, an aryloxy group, an acyl group, an acylamino group, a nitro group, a cyano group, an oxycarbonyl group, a hydroxy group, a carboxy group, a sulfo group, a ureido group, a sulfonamido group, a sulfamoyl group, a carbamoyl group, an acyloxy group, an amino group, a carbonic acid ester group and a sulfone group.

19. A silver halide photographic light-sensitive material as claimed in claim 2, wherein Y is an electron donating group.

20. A silver halide photographic light-sensitive material as claimed in claim 2, wherein Y is an electron attracting group.

21. A silver halide photographic light-sensitive material as claimed in claim 1, wherein the blocked photographic agent is present in a silver halide emulsion layer.

22. A silver halide photographic light sensitive material as claimed in claim 1, wherein the blocked photographic agent is an antifoggant and the blocked photographic agent is contained in the photographic material in an amount of $10^{-8}$ to $10^{-1}$ mole per mole of silver in the silver halide emulsion.

23. A silver halide photographic light-sensitive material as claimed in claim 1, wherein the blocked photographic agent is a development restrainer and the blocked photographic agent is contained in the photographic material in an amount of $10^{-8}$ to $10^{-1}$ mole per mole of silver in the silver halide emulsion.

24. A silver halide photographic light-sensitive material as claimed in claim 1, wherein the blocked photographic agent is a developing agent and the blocked photographic agent is contained in the photographic material in an amount of $10^{-2}$ to 10 mole per mole of silver in the silver halide emulsion.

25. A silver halide photographic light-sensitive material as claimed in claim 1, wherein the blocked photographic agent is an auxiliary developer of a pyrazolidone type and the blocked photographic agent is contained in the photographic material in an amount of $10^{-4}$ to 10 mole per mole of silver in the silver halide emulsion.

26. A silver halide photographic light-sensitive material as claimed in claim 1, wherein the blocked photographic agent is a fogging agent and the blocked photographic agent is contained in the photographic material in an amount of $10^{-2}$ to $10^{-6}$ mole per mole of silver in the silver halide emulsion.

27. A silver halide photographic light sensitive material as claimed in claim 1, wherein the blocked photographic agent is a silver halide solvent and the blocked photographic agent is contained in the photographic material in an amount of $10^{-3}$ to 10 mole per mole of silver in the silver halide emulsion.

28. A silver halide photographic light-sensitive material as claimed in claim 1, wherein the blocked photographic agent is a bleach accelerating agent and the blocked photographic agent is contained in the photographic material in an amount of $10^{-5}$ to $10^{-1}$ mole per mole of silver in the silver halide emulsion.

29. A silver halide photographic light sensitive material as claimed in claim 1, wherein the blocked photographic agent is a dye and the blocked photographic agent is contained in an amount of $10^{-3}$ to 1 mole per mole of silver in the silver halide emulsion.

30. A silver halide photographic light sensitive material as claimed in claim 1, wherein the blocked photographic agent is a coloring material for color diffusion transfer photographic light-sensitive material and the blocked photographic agent is contained in an amount of $10^{-3}$ to 1 mole per mole of silver in the silver halide emulsion.

31. A silver halide photographic light-sensitive material as claimed in claim 1, wherein the photographic material is a silver halide color photographic light-sensitive material containing a color forming coupler.

32. A silver halide photographic light-sensitive material as claimed in claim 1, wherein the photographic material is a color diffusion transfer silver halide photographic light-sensitive material containing a dye-image providing material.

33. A silver halide photographic light-sensitive material as claimed in claim 1, wherein the photographic material is a silver halide color photographic light-sensitive material containing a bleachable dye.

34. A silver halide photographic light-sensitive material as claimed in claim 1, wherein the photographic material is a black and white silver halide photographic light-sensitive material which forms a silver image upon black and white development.

* * * * *